(12) United States Patent
Natbony

(10) Patent No.: US 12,109,098 B1
(45) Date of Patent: Oct. 8, 2024

(54) SECURE TAMPON

(71) Applicant: THINK DO IT, Marietta, GA (US)

(72) Inventor: Suzanne Raina Natbony, Los Angeles, CA (US)

(73) Assignee: THINK DO IT, Marietta, GA (US)

( * ) Notice: Subject to any disclaimer, the term of this patent is extended or adjusted under 35 U.S.C. 154(b) by 806 days.

(21) Appl. No.: 17/222,770

(22) Filed: Apr. 5, 2021

Related U.S. Application Data

(63) Continuation-in-part of application No. 17/020,721, filed on Sep. 14, 2020, and a continuation-in-part of application No. 16/773,756, filed on Jan. 27, 2020, now Pat. No. 11,529,270, which is a continuation-in-part of application No. 15/648,380, filed on Jul. 12, 2017, now Pat. No. 10,835,633.

(60) Provisional application No. 62/379,404, filed on Aug. 25, 2016.

(51) Int. Cl.
| | |
|---|---|
| *A61F 13/20* | (2006.01) |
| *A61F 13/34* | (2006.01) |
| *A61F 13/82* | (2006.01) |
| *A61F 13/84* | (2006.01) |
| *A61F 15/00* | (2006.01) |

(52) U.S. Cl.
CPC ............ *A61F 13/82* (2013.01); *A61F 13/202* (2013.01); *A61F 13/34* (2013.01); *A61F 13/8405* (2013.01); *A61F 2013/8497* (2013.01); *A61F 15/002* (2013.01)

(58) Field of Classification Search
CPC ...... A61F 13/20; A61F 13/202; A61F 13/204; A61F 13/34; A61F 13/58; A61F 13/83
See application file for complete search history.

(56) References Cited

U.S. PATENT DOCUMENTS

| | | | |
|---|---|---|---|
| 3,037,506 A * | 6/1962 | Penksa ................. | A61F 13/505 604/385.18 |
| 6,679,868 B2 * | 1/2004 | Kostadimas ........... | A61F 13/34 604/385.18 |
| 7,344,732 B2 * | 3/2008 | Gehling .............. | A61F 13/2074 424/431 |
| 9,301,883 B2 * | 4/2016 | Donovan ................ | A61F 13/34 |
| 9,326,897 B2 * | 5/2016 | Ito ............................ | A61F 13/26 |
| 2002/0068918 A1 * | 6/2002 | Durel-Crain .......... | A61F 13/204 604/385.18 |
| 2008/0154221 A1 * | 6/2008 | Thornton .......... | A61F 13/55175 604/11 |

* cited by examiner

*Primary Examiner* — Catharine L Anderson
(74) *Attorney, Agent, or Firm* — John Weatherspoon

(57) ABSTRACT

The present invention relates to novel and secure tampons that overcome the problems associated with conventional non-secure tampons, and methods of using the novel and secure tampons.

30 Claims, 18 Drawing Sheets

510

SECURE TAMPON

CROSS REFERENCE TO RELATED APPLICATIONS

This U.S. continuation-in-part patent application claims priority to pending U.S. patent application Ser. No. 17/020,721, filed Sep. 14, 2020 and pending U.S. patent application Ser. No. 16/773,756, filed Jan. 27, 2020, which in turn claim priority to U.S. patent application Ser. No. 15/648,380, filed Jul. 12, 2017, which in turn claims priority to U.S. provisional patent application Ser. No. 62/379,404 filed Aug. 25, 2016.

FIELD OF THE INVENTION

The present invention relates to novel and secure tampons that overcome the problems associated with conventional non-secure tampons, and methods of using the novel and secure tampons.

BACKGROUND OF THE INVENTION

Menstruation products compose an estimated 15-billion-dollar market. The average woman uses about 10,000 sanitary products during her lifetime. Most women use tampons and women younger than 41 are far more likely to use them. Sometimes women wear both a tampon and a pad at the same time, for extra protection. About one in four women in perimenopause (ages 48 to 54) use tampons and/or pads between their periods. Tampons, which have been around since the 1930s, are the most popular choice of feminine protection for women younger than 41. Women often choose tampons for greater physical freedom during their period. Women usually change tampons at least every four to eight hours, typically using the least absorbent type to manage menstrual flow. Tampons are not recommended in between periods. There was a connection between conventional, non-secure superabsorbent tampons and an outbreak of toxic shock syndrome (TSS) in the 1980s, and these "hyper absorbable" tampons were taken off the market. In addition to pads and tampons, menstruation cups and Thinx® underwear are other types of menstruation products. In the 1980s, Always® became an industry leader by introducing "wings" on pads. Many women prefer pads with wings over pads without wings. However, with conventional non-secure tampons, women sometimes forget about the tampon and actually "lose" the tampon inside of them, which can be very dangerous. Losing a tampon is associated with many significant problems for women, including but not limited to toxic shock syndrome (TSS), a life-threatening disease. Further, many women and, especially younger girls, will not wear tampons or avoid them because of not only the fear of a "lost tampon," but also the association with TSS.

Most conventional, non-secure tampons have a string for removal; however with conventional, non-secure tampons there is no adhesive element that is attached to the string. Therefore, with conventional, non-secure tampons, the string is sometimes lost, for instance when the string gets stuck or trapped or lodged within the vagina. This loss of the string is problematic and dangerous to the woman's health. The use of a conventional, non-secure tampon is therefore often associated with many significant problems for women, including but not limited to toxic shock syndrome (TSS), a life-threatening disease. In addition to TSS, the use of conventional, non-secure tampons can also cause other serious problems including, but not limited to, urinary tract infections, urogenital infections, vaginal ulcers and unwanted mucosal changes, each of which can be very detrimental. Lost tampons can also cause anxiety in women as treatment for lost tampons can occur not only with an OBGYN, but also at emergency rooms and urgent care centers.

Therefore, while many non-secure, conventional tampons have strings attached, these non-secure, conventional tampons pose significant problems for women since the string is often lost or gets lodged in the vagina.

There is therefore a long-felt, significant and unmet need in the art for improved, secure tampons and methods of using secure tampons.

Additional aspects of the invention will become apparent in view of the following description and associated figures.

SUMMARY OF THE INVENTION

Certain embodiments of the present invention provide a secure tampon, comprising an absorbent object which is securely attached to at least one or more connector elements, and further wherein the one or more connector elements are safely and securely attached to at least one or more adhesive elements.

Other embodiments of the present invention provide a secure tampon, wherein at least one or more connector elements comprise any type of safe and non-toxic string, thread, filament, fiber, microfiber, yarn or other type of safe and non-toxic connective element.

Other embodiments of the present invention provide a secure tampon, wherein at least one or more adhesive elements can be securely, but temporarily attached to at least one area of the tampon wearer's body. The tampon wearer can then easily and safely remove the one or more adhesive elements at any time when needed or desired.

Other embodiments of the present invention provide a secure tampon, wherein at least one or more adhesive elements comprise any type of safe and non-toxic tape, adhesive material, waterproof tape, medical adhesive tape, pressure sensitive adhesive tape, surgical tape, paper tape, sticker or any combination thereof.

Other embodiments of the present invention provide a secure tampon, wherein at least one or more backings of the adhesive elements comprise cloth, waterproof material, paper, pressure-sensitive tape, micropore adhesive material, nonwoven, breathable films such as polyurethane or any combination thereof.

In other embodiments, one or more adhesive elements comprise hydrocolloid, acrylic, polyurethane, silicone, or any combination thereof.

In still other embodiments, an adhesive element comprises three parts including a liner (which is removed and discarded), an adhesive substance and a backing (the part of the adhesive element that does not stick, and which is substrate). In preferred embodiments, the backing of an adhesive element is breathable and includes, for example, cloth or nonwoven, breathable films such as polyurethane.

Other embodiments of the present invention provide a secure tampon, wherein one or more adhesive elements securely but temporarily attach to any area of skin surrounding the vagina, any part of the leg or legs, inner thigh, or any area of the skin covering the pubic bone. The invention also contemplates attachment to hair without being uncomfortable to remove. The tampon wearer can easily and safely remove the one or more adhesive elements at any time when needed or desired.

Other embodiments of the present invention provide a self-assembled secure tampon comprising an absorbent object which is already securely attached to at least one or more connector elements, and further wherein the one or more connector elements are safely and securely attached to at least one or more adhesive elements.

Other embodiments of the present invention provide a secure tampon comprising at least one adhesive means for attaching the secure tampon to at least one area of a woman's body.

Other embodiments of the present invention provide a secure tampon, wherein the means for attaching the secure tampon to at least one area of a woman's body comprises the use of tape or other adhesive material that is attached to at least one or more connector elements.

Certain embodiments of the present invention include a generally rectangular-shaped adhesive element, and other embodiments include a T-shape adhesive element.

Other embodiments and further details regarding various aspects of the present invention are set forth in the following description and claims. It is to be understood that the invention is not limited in its application to the details set forth in the following description and claims, but is capable of other embodiments and of being practiced or carried out in various ways.

BRIEF DESCRIPTION OF THE DRAWINGS

These and/or other aspects and advantages of the invention will become apparent and more readily appreciated from the following description of the embodiments, taken in conjunction with the accompanying drawings of which.

Figure 1:
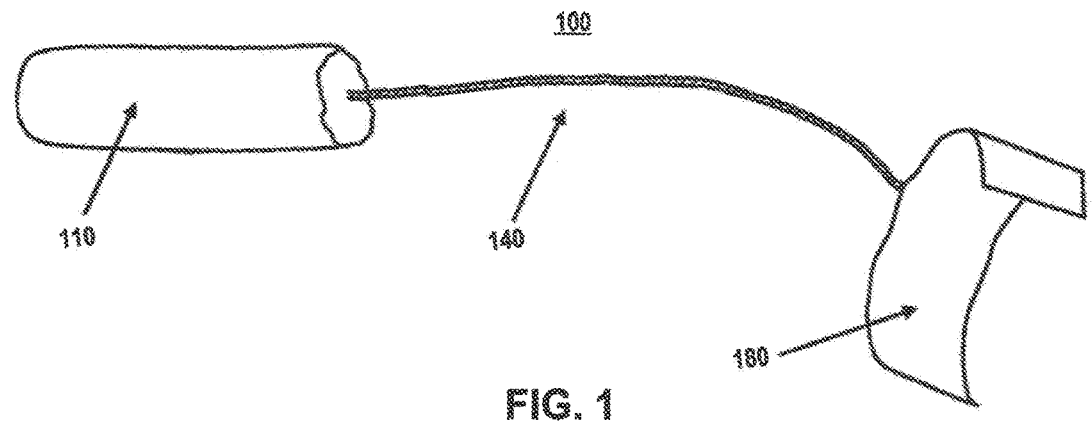
FIG. 1 depicts one preferred embodiment of a secure tampon 100 according to the present invention.

These figures, as described herein, show representative embodiments of the present invention, and these representative embodiments do not limit the scope of the invention in any way.

DESCRIPTION OF PREFERRED EMBODIMENTS

Although the detailed description herein contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention. While embodiments are described in connection with the drawings and related descriptions, there is no intent to limit the scope to the embodiments disclosed herein. On the contrary, the intent is to cover all alternatives, modifications, and equivalents. In alternative embodiments, additional devices, or combinations of illustrated devices, may be added to, or combined, without limiting the scope to the embodiments disclosed herein.

As used herein, the phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise.

Unless defined otherwise, all technical terms used herein have the same meaning as commonly understood by one of ordinary skill in the art.

As used herein, the term "secure tampon" is understood, in accordance with the present invention, to refer to any absorbent object which is securely attached to at least one or more connector elements, and further wherein the one or more connector elements are, in turn, safely and securely attached to at least one or more adhesive elements. The one or more adhesive elements comfortably, securely and safely attach to at least one area of the tampon wearer's body including but not limited to any area of skin surrounding the vagina, any part of the leg (or legs), inner thigh, or any area of the skin covering the pubic bone, with or without hair, and preferably as close as possible to the vagina, but still outside of it, such as on the labia majora. The tampon wearer can easily and safely remove the one or more adhesive elements at any time when needed or desired.

According to one preferred embodiment of the present invention, a secure tampon is provided that includes at least one adhesive means for attaching the secure tampon to at least one area of a woman's body. One such preferred adhesive means for attaching the tampon to at least one area of a woman's body is the use of tape or other adhesive material that is attached to at least one or more connector elements.

In a preferred embodiment, the secure tampon of the present invention would be worn during menstruation for a time period of up to eight hours, as well as when the tampon is substantially saturated or completely saturated. Use of the secure tampons of the present invention allows the wearer of the tampon to prevent loss of the tampon during use and address and overcome other disadvantages of conventional, non-secure tampons.

It is to be understood that females of any suitable age of menstruation or spotting can use the secure tampons of the present invention. This includes, but is not limited to, adolescent women who are starting to experience menstrual cycles or menstruation, women of any age who are already experiencing menstrual cycles or menstruation, and women in perimenopause. The secure tampon of the present invention will preferably be used by women from the age of menstruation to menopause, who either use tampons or who have never before used tampons because of concerns and problems associated with the use of conventional, non-secure tampons.

The terms "female" and "woman" and "women" may be used interchangeably herein in this description.

As used herein, the term "absorbent object" is intended to include, but is not limited to, any object that functions as a tampon, such as a plug or other mass of soft material, which can be safely inserted into a female's vagina to absorb menstrual blood, e.g., during a menstrual period. The absorbent object of the present invention can be made of any suitable material including, but not limited to, cotton, rayon, a blend of cotton and rayon, or any other suitable material or blend of materials. The absorbent object of the present invention can also include any organic material or combination of organic materials, such as for example materials in an "organic" tampon.

As used herein, the term "absorbent" is intended to include any degree of absorbency, including but not limited to partial absorbency, substantial absorbency or complete absorbency, wherein "absorbency" refers to the ability of the absorbent object to absorb or soak up menstrual blood, e.g., during a menstrual period.

In accordance with the present invention, one preferred embodiment of an absorbent object is an applicator tampon which generally expands axially (i.e., increases in length) when inserted into the vagina of the tampon wearer.

In accordance with the present invention, another preferred embodiment of an absorbent object is a tampon which generally expands radially (i.e. increases in diameter) when inserted into the vagina of the tampon wearer.

The secure tampon of the present invention may be scented or unscented, and can have any desired size, shape and dimensions, and can be designed to have any color (or combination of colors), as well as have any desired thickness. One example of a secure tampon may be a cylinder-like shape, so it can be easily inserted into the vagina. The secure tampon absorbs a woman's menstrual flow, or blood, before the menstrual flow has a chance to leave the body. The secure tampons may come in different sizes and have different absorbances.

The secure tampon of the present invention also provides users with many other significant advantages and meets another very important and long-felt need that was never possible with conventional tampons. With conventional tampons, women often forget that it is time to discard a tampon after they have used it for a certain period of time (for example, after they have used a tampon for eight hours) and to replace it with a new tampon. To overcome this problem, and according to one preferred embodiment of the present invention, a secure tampon of the present invention can be designed such that an adhesive element (for example, soft tape) has the ability to change color to show that it is time to discard a tampon after the tampon has been used by the user for a certain period of time. For example, an adhesive element (as shown and described in the figures) is first applied by a woman to secure a tampon to at least one part of the woman's body. After the woman has used the tampon for a certain period of time, for example eight hours, the adhesive element then visibly changes color which acts as a visible sign to indicate to the woman that it is time to discard the used tampon and replace it with a new tampon.

Moreover, females can use the secure tampons of the present invention when wearing any kind of undergarment or bathing suit, including but not limited to thong panties, and other types of underwear. According to a preferred embodiment, a female can use the secure tampon for no more than eight hours, as recommended by the FDA, such that secure tampons have been tested to confirm that the secure tampon remains secure for eight hours, even with swimming and showering.

In accordance with the present invention, examples of at least one or more connector elements include, but are not limited to, any type of safe and non-toxic string, thread, filament, fiber, microfiber, yarn or other type of safe and non-toxic connective element. Examples of representative materials that can be used to form safe and non-toxic connective elements include, but are not limited to, safe and non-toxic types of thread, cotton, rubber or plastic. Preferably the safe and non-toxic connective elements are elongated and resistant to tearing.

As shown and described in more detail herein, the connector elements can also be manufactured to include a series of long, tear-resistant fibers or other elongated elements that (i) extend longitudinally throughout the length of each connector element, and (ii) extend longitudinally throughout the length of the tampon, and (iii) also extend longitudinally throughout the length of the one or more adhesive elements. These elongated elements thus provide additional reinforcement and strength and thus help prevent loss of the tampon.

In accordance with the present invention, examples of at least one or more adhesive elements include, but are not limited to, any type of safe and non-toxic tape, adhesive material, such as waterproof tape, medical adhesive tape, pressure sensitive adhesive tape, surgical tape, paper tape, or any combination thereof, and can be made of any number of different types of materials, such as for example, cloth, waterproof material, sticker, tape, paper, pressure-sensitive tape, any type of adhesive, any type of adhesive material, any type of glue or any combination thereof, to name just a few examples. One non-limiting example of an adhesive material is a micropore adhesive material.

In other embodiments, one or more adhesive elements comprise hydrocolloid, acrylic, polyurethane, silicone, or any combination thereof.

In still other embodiments, an adhesive element comprises three parts including a liner (which is removed and discarded), an adhesive substance and a backing (the part of the adhesive element that does not stick, and which is substrate). In preferred embodiments, the backing of an adhesive element is breathable and includes, for example, cloth or nonwoven, breathable films such as polyurethane.

An adhesive element can have any desired or suitable size, shape, thickness and other dimensions. For example, an adhesive element can have a thickness of about 0.1 centimeter, or about 0.2 centimeters, about 0.3 centimeters, about 0.4 centimeters, or about 0.5 centimeters. These are all non-limiting examples and do not limit the scope of the invention in any way.

The present invention also contemplates that the adhesive element can have any desired shape, any desired size, any desired thickness, any other desired dimension, and can be made of any desired material or combination of materials.

Some non-limiting examples of possible materials that can be used to make an adhesive element include, for example, any possible natural, organic, synthetic and non-synthetic material, or any combination thereof.

Regarding any desired shape of an adhesive element, an adhesive element can for example have a shape that is generally round, circular, oval, elliptical, square, rectangular, triangular, or any other shape including but not limited to a semicircle, nonagon, octagon, heptagon, hexagon, pentagon, decagon, prism-shape, pyramid-shape, cone-shape, any other type of polygon, equilateral triangle, right triangle, scalene triangle, obtuse triangle, acute triangle, isosceles triangle, parallelogram, rhombus, kite, quadrilateral, trapezium, trapezoid, heart-shape, diamond-shape, crescent-shape, flower-shape, star-shape, flower-shape, rainbow-shape, any alphabet letter shape, animal-shape, icosahedron or a dodecahedron. In another embodiment, an adhesive element can also generally be in the shape of a dot, wherein the "dot-shaped" adhesive element has any desired radius or diameter. These are of course all non-limiting examples and do not limit the scope or number of other possible shapes of an adhesive element.

The secure tampons of the present invention will significantly help prevent loss of a tampon during use by a woman, and also significantly help to prevent associated health and medical problems associated with a lost tampon (such as, for example, loss of a tampon due to loss of the string attached to the tampon). The secure tampons of the present invention may be useful in helping to prevent toxic shock syndrome (TSS).

As discussed herein, most conventional, non-secure tampons have a string, however with conventional, non-secure tampons there is no adhesive element that is attached to the string. Therefore, with conventional, non-secure tampons, the string is sometimes lost, for instance when the string gets stuck or trapped or lodged within the vagina. This loss of the string is very problematic and dangerous to the woman's health. The use of a conventional, non-secure tampon is therefore often associated with many significant problems for women, including but not limited to toxic shock syndrome (TSS), a life-threatening disease. In addition to TSS, the use of conventional, non-secure tampons can also cause, or be associated with, other serious problems including, but not limited to, urinary tract infections, urogenital infections, vaginal ulcers and unwanted mucosal changes, each of which can be very detrimental. Lost tampons can also cause anxiety in women as treatment for lost tampons can occur not only with an OBGYN, but also at emergency rooms and urgent care centers.

In accordance with the present invention, the adhesive element (e.g. soft tape) on the secure tampon secures the tampon to at least one part of a woman's body, so she sees it and will not forget about it or lose the string inside her. Thus, the secure tampon of the present invention reduces the risk of contracting TSS and other complications, and also reduces the risk of urinary tract infections, urogenital infections, vaginal ulcers and unwanted mucosal changes. The secure tampon of the present invention also offers improved hygiene because the string will not get lost near the behind, thus minimizing e-coli bacterial infections. The adhesive element (e.g. soft tape) functions like an anchor to the body so a woman wearing it does not lose the tampon or forget about it. Further, some women complain about the string getting caught on underwear or clothing and causing the tampon to shift while walking and even get tugged out while walking. Other women do not like how the string can hang out of a bikini, underwear or skirt, all of which can be embarrassing. To prevent the string hanging out, some women cut the string shorter, but then become even more concerned about losing it with the shorter string. Also, some menstruating women inquire about being able to have sex with a tampon to prevent a bloody mess. The secure tampon can enable sex without a mess because the tape or other adhesive element (when adhered to a part of the woman's body) keeps the tampon intact.

Prior to the present invention, there has been no solution for preventing the loss of a tampon and there have been no tampons that allow a woman to securely tape or otherwise attach or securely fix the tampon to her body. Prior to the present invention, there have been no preventive measures that enable a woman to reliably prevent the loss of her tampon.

The secure tampon of the present invention is a revolutionary product for the feminine hygiene market. The secure tampon of the present invention enables younger women, especially pubescent girls who are afraid to use tampons or whose parents might not allow it, to use tampons.

According to one embodiment, the present invention also contemplates the use of one or more safe and non-toxic liquid adhesives. For example, a secure tampon in accordance with the present invention can include any absorbent object which is securely attached to at least one or more connector elements, and further wherein the one or more connector elements are, in turn, safely and securely attached to at least one or more adhesive elements. The one or more adhesive elements comfortably, securely and safely attach to at least one area of the tampon wearer's body including but not limited to any area of skin surrounding the vagina, any part of the leg (or legs), inner thigh, or any area of the skin covering the pubic bone, with or without hair, and preferably as close as possible to the vagina, but still outside of it, such as on the labia majora. The tampon wearer can easily and safely remove the one or more adhesive elements at any time when needed or desired. The tampon wearer can also use one or more safe and non-toxic liquid adhesives (including but not limited to liquid adhesives in the form of gels, liquids, ointments or creams) which can be used in combination with the one or more adhesive elements. The one or more safe and non-toxic liquid adhesives can be safely applied by the tampon wearer to at least one area of the tampon wearer's body including but not limited to any area of skin surrounding the vagina, any part of the leg (or legs), inner thigh, or any area of the skin covering the pubic bone, with or without hair, and preferably as close as possible to the vagina, but still outside of it, such as on the labia majora. The one or more safe and non-toxic liquid adhesives are all previously determined to be safe for use on human skin as determined by dermatologists and other healthcare and regulatory authorities. The one or more safe and non-toxic liquid adhesives can also have any desired thickness, viscosity, color and other desired characteristics. In one embodiment, the one or more safe and non-toxic liquid adhesives also have the ability to change color to show that it is time to discard a tampon after the tampon has been used for a certain period of time (for example, after a woman has used a tampon for eight hours), The one or more safe and non-toxic liquid adhesives can also be scented or unscented, and are preferably formulated not to penetrate the skin. The one or more safe and non-toxic liquid adhesives can also be manufactured and stored, packaged and sold in a separate package or container. The one or more safe and non-toxic liquid adhesives can also preferably be easily and safely removed at any time as desired by the tampon wearer.

In a preferred embodiment, a safe and non-toxic liquid adhesive can be applied directly to the end portion of one or more connector elements (for example, a safe and non-toxic liquid adhesive can be applied directly to the end portion of a string), and in this embodiment no additional adhesive element is used by the tampon wearer. In this embodiment, the safe and non-toxic liquid adhesive keeps the tampon securely in place when the tampon wearer safely, securely and reversibly attaches the end portion of the one or more connector elements (covered with the liquid adhesive) to at least one area of the tampon wearer's body including but not limited to any area of skin surrounding the vagina, any part of the leg (or legs), inner thigh, or any area of the skin covering the pubic bone, with or without hair, and preferably as close as possible to the vagina, but still outside of it, such as on the labia majora. The safe and non-toxic liquid adhesive can be easily and safely removed at any time as desired by the tampon wearer.

According to one embodiment, the present invention encompasses an already self-assembled secure tampon with tape or other adhesive element attached to the string that is already assembled and ready to use. By way of non-limiting example, a woman can purchase a package that includes an already self-assembled secure tampon (or, alternatively, a package containing multiple self-assembled secure tampons) with or without applicators. Moreover, each already self-assembled secure tampon can be designed either with or without an applicator, thus giving consumers more options. In a preferred embodiment, in which each already self-assembled secure tampon is designed without an applicator, each of the already self-assembled secure tampons includes an absorbent object (such as, for example, an organic tampon) which is already securely attached to at least one or more connector elements, and further wherein the one or more connector elements are, in turn, safely and securely attached to at least one or more adhesive elements.

According to another embodiment, the present invention encompasses a "do-it-yourself" kit for self-assembly of a secure tampon, either with or without an applicator, thus giving consumers more options. In a preferred embodiment, a "do-it-yourself" kit for self-assembly of a secure tampon (in one case, without an applicator) includes an absorbent object (such as, for example, an organic tampon), which is already securely attached to at least one or more connector elements. The "do-it-yourself" kit also separately includes at least one or more adhesive elements (for example, two pieces of tape that a woman can use with any tampon with a string). When someone purchases the kit, they can very easily securely attach the one or more adhesive elements to the at least one or more connector elements, wherein the one or more connector elements are already securely attached to the absorbent object.

According to yet another embodiment, the present invention encompasses another type of "do-it-yourself" kit that includes just one or two adhesive elements. By way of non-limiting example, when a woman purchases this kit, she can very easily attach the one or two adhesive elements to one of her own tampons, e.g., by securely attaching the one or more adhesive elements to a string that is already attached to the tampon. In this manner, she can form her own secure tampon for safe, secure and reliable use.

According to one preferred embodiment, shown in FIG. 1, a secure tampon 100 comprises an absorbent object 110 (the absorbent object 110 is shown on the left side of FIG. 1) which is securely attached to at least one or more connector elements 140 (e.g., the connector elements in FIG. 1 are the cords or strings), and further wherein the one or more connector elements 140 are, in turn, safely and securely attached to at least one or more adhesive elements 180 (the adhesive element 180 is the piece of flexible tape which is shown on the right side of FIG. 1). The one or more adhesive elements 180 can be any size and shape. The one or more adhesive elements 180 (for example, the piece of flexible tape which is shown on the right side of FIG. 1) comfortably, securely, and safely attach to at least one area of the tampon wearer's body. The tampon wearer can then easily and safely remove the one or more adhesive elements 180 at any time when needed or desired.

Figure 2:
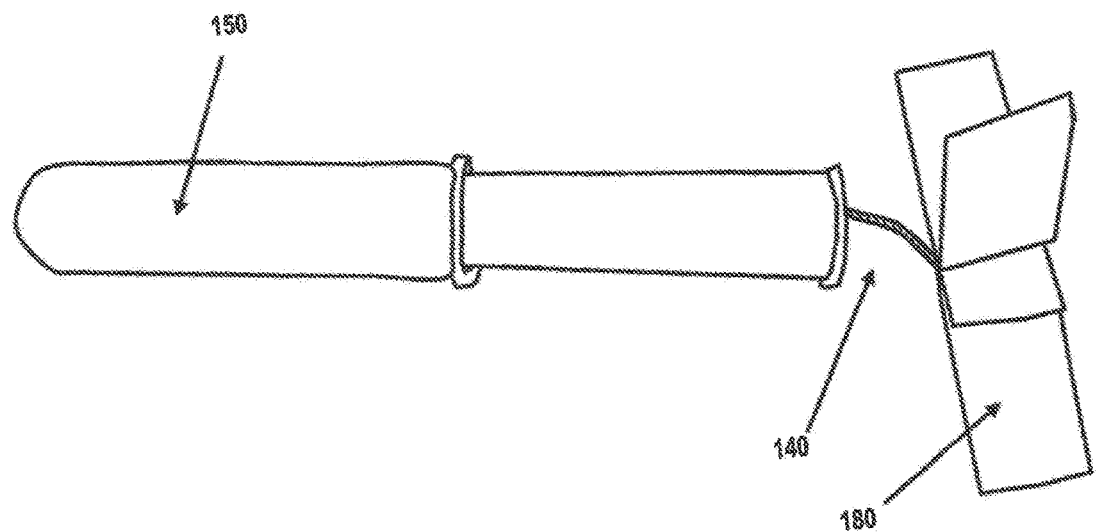
FIG. 2 depicts one preferred embodiment of a secure tampon with an applicator 150.

It is to be understood that, in accordance with the present invention, secure tampons can be used with or without an applicator, such as a built-in applicator. Referring to FIG. 2, many women may prefer to use a secure tampon 100 with an applicator 150. Any suitable applicator can be used to place the secure tampon 100. In a preferred embodiment, the present invention includes an absorbent object 110 itself that a woman inserts into her vagina, and an applicator 150 (e.g. a plastic applicator) that the woman uses to insert the absorbent object 110 in her vaginal opening. In one example, the woman places the absorbent object 110 in her vaginal opening. One such example of a secure tampon 100 with an applicator 150, in accordance with the present invention, is shown in FIG. 2.

According to a preferred embodiment, the secure tampon 100, which comprises an absorbent object 110, is securely attached to at least one or more connector elements 140. By way of example, the connector elements 140, as shown in FIG. 1 and FIG. 2, can include one or more cords or strings, or other type of connecting material. The one or more connector elements 140 are, in turn, safely and securely attached to at least one or more adhesive elements 180. By way of example, representative examples of the adhesive elements 180 are shown on the right side of FIG. 1 and FIG. 2. The one or more adhesive elements 180 comfortably, securely and safely attach to at least one area of the tampon wearer's body. The tampon wearer can safely remove the one or more adhesive elements 180 at any time.

In another embodiment, the one or more connector elements 140 are, in turn, safely and securely attached to at least one or more adhesive elements 280. Representative examples of adhesive elements 280 are also described in more detail below. The one or more adhesive elements 280 comfortably, securely and safely attach to at least one area of the tampon wearer's body. The tampon wearer can safely remove the one or more adhesive elements 280 at any time.

Figure 3:
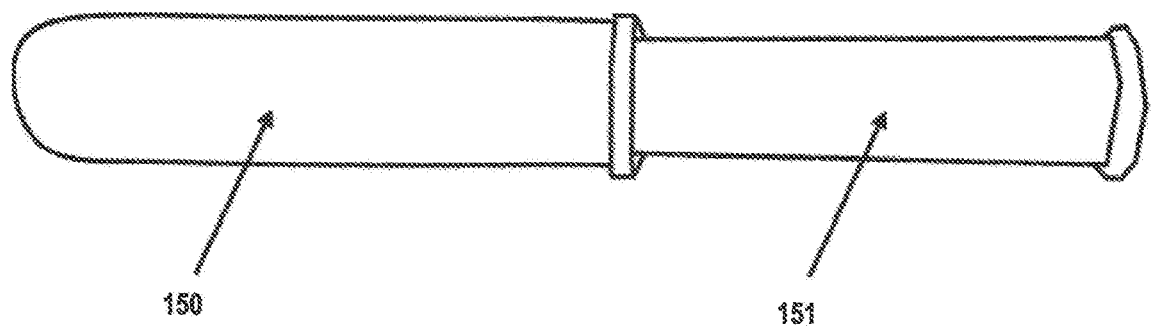
FIG. 3 depicts one preferred embodiment wherein the elements of a secure tampon are conveniently stored within the applicator 150.

According to one preferred embodiment, the connector elements 140 and adhesive elements 180 can be conveniently stored within the applicator 150, as shown by way of example in FIG. 3. As depicted in FIG. 3, the connector elements 140 and adhesive elements 180 are not visible because the connector elements 140 and adhesive elements 180 are conveniently rolled up inside the right side 151 of the applicator.

In another example, the connector elements 140 and adhesive elements 280 can be conveniently stored within the applicator 150.

Figure 4:
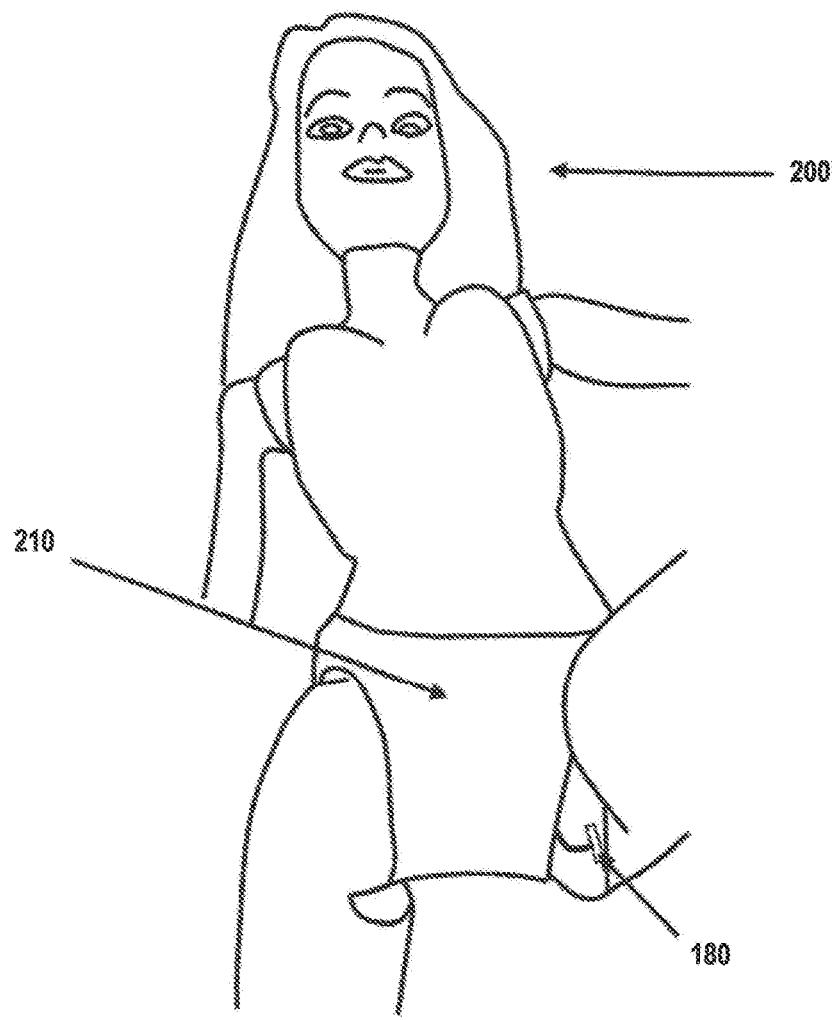
FIG. 4 depicts one embodiment of a woman wearing underwear after application of a secure tampon of the invention.

By way of non-limiting example, referring to FIG. 4, after a woman 200 wearing underwear 210 has inserted an absorbent object 110 into her vagina, she then safely and securely places one or more adhesive elements 180 to the skin surrounding her vagina, such as the inner thigh, as shown by the adhesive element 180 that the woman has adhered to the skin surrounding her vagina, as shown in FIG. 4.

According to another non-limiting example, after a woman 200 wearing underwear 210 has inserted an absorbent object 110 into her vagina, she then safely and securely places one or more adhesive elements 280 to the skin surrounding her vagina. The woman can safely remove the one or more adhesive elements 280 at any time.

Figure 5:
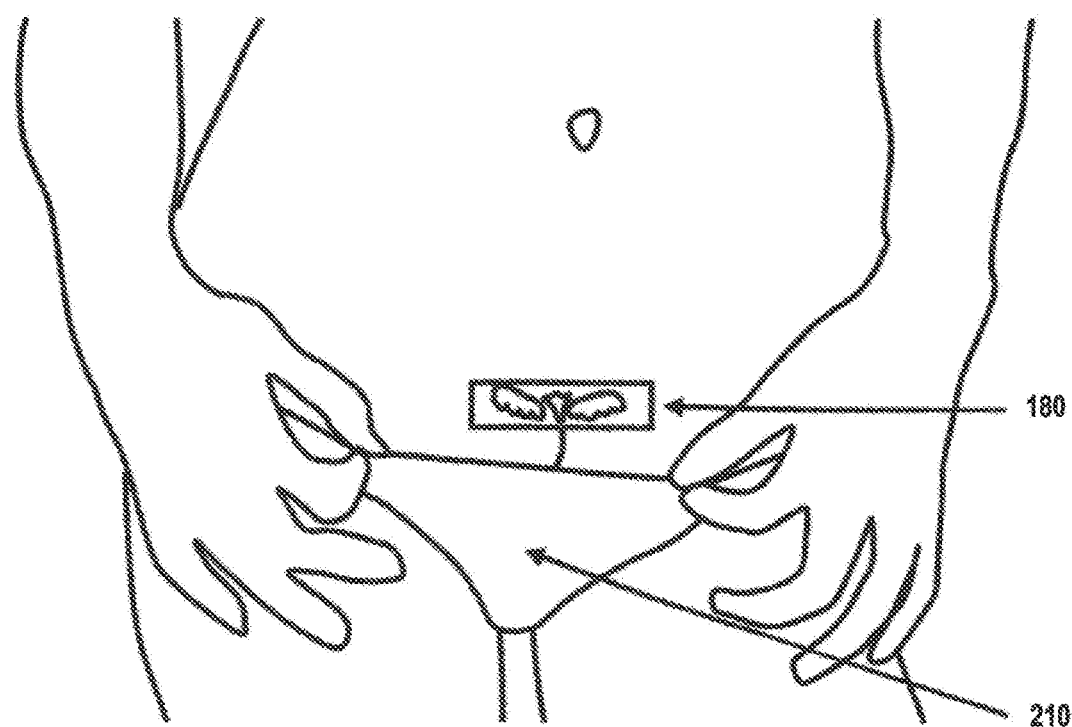
FIG. 5 shows a representative close-up view of the mid-region of a woman wearing underwear after applying a secure tampon of the present invention. The present invention also contemplates a design printed on the tape, such as wings, as shown on 180.

Also, by way of non-limiting example, FIG. 5 shows a representative close-up view of the mid-region of a woman 200 wearing underwear 210 after applying a secure tampon 100 of the present invention.

As shown in FIG. 5, the woman has safely and securely adhered an adhesive element 180 to the skin on her pelvic region. This is shown, by way of example, by the adhesive tape (one example of an adhesive element 180) that the woman has adhered to her skin, as shown in FIG. 5. An adhesive element 180 can also have any aesthetic design, as shown by the design on the tape shown in FIG. 5. The woman can safely remove the adhesive element 180 at any time.

An adhesive element 180 can also have any type of logo, pattern, image, etc that is displayed on the adhesive element 180. A logo, pattern, image, etc can, for example, include one or more designs or combination of designs, one or more figures or combination of figures, one or more shapes or combination of shapes, one or more letters and/or numbers or any combination of letters and/or numbers. In other embodiments, the logo, pattern, image, etc. can also incorporate one or more colors or combination of colors, including the ability to change color to show that it's time to discard, and can also incorporate any other design features or elements that can be conceived of by an artist, designer, manufacturer, etc.

As shown in FIG. 5, the adhesive element (for instance, soft tape) on the secure tampon secures the tampon to a woman's body, and she therefore also sees the adhesive element and will not forget about it or lose the string (or other connective element) inside her. The secure tampon of the present invention also offers improved hygiene because the string will not get lost near the behind, possibly minimizing *E. coli* bacterial infections.

Representative Adhesive Element that is Generally Rectangular in Shape

Figure 6:
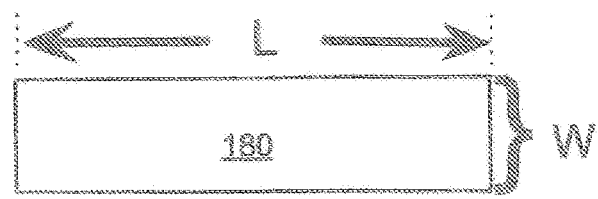
FIG. 6 depicts one preferred embodiment of an adhesive element that is generally rectangular in shape. The present invention also contemplates that the adhesive element can be round or any other shape, in a similar size.

According to one preferred embodiment, and by way of non-limiting example, an adhesive element can be generally rectangular in shape (for instance, designed as a rectangular piece of tape) as shown for example in FIG. 6. When the adhesive element is a rectangular piece of tape, the rectangular piece of tape can have any shape and size, and can also have any suitable thickness. For example, an adhesive element can have a thickness of about 0.1 centimeter, or about 0.2 centimeters, about 0.3 centimeters, about 0.4 centimeters, or about 0.5 centimeters. These are all non-limiting examples and do not limit the scope of the invention in any way.

FIG. 6 depicts one preferred embodiment of an adhesive element that could be generally rectangular in shape. As shown in FIG. 6, adhesive element 180 has a length "L" which is measured as the total distance along the horizontal edge of the adhesive element 180 (this distance along the horizontal edge is measured as the length "L" between the two vertical dotted lines shown in FIG. 6; each arrow in FIG. 6 points to one of the two vertical dotted lines).

Also, as shown in FIG. 6, adhesive element 180 has a width "W" which is measured as the total distance along the vertical edge of the adhesive element 180 as clearly depicted in FIG. 6.

In a preferred embodiment, an adhesive element 180 preferably has a size that is anything less than 3 inches in length by 3 inches in width.

Some other non-limiting examples of dimensions of a generally rectangular adhesive element 180 are listed below:
  0.1 inches in width and 1.0 inch in length
  1.0 inch in width and 2.5 inches in length
  1.5 inches in width and 3.0 inches in length
  0.75 inches in width and 3.0 inches in length
  $^{11}/_{16}$ inches in width and 2.5 inches in length
  1.25 inches in width and 2.0 inches in length An adhesive element 180 can have many other dimensions. Here are some other non-limiting examples of dimensions of a generally rectangular adhesive element 180:
  0.1 inches in length and 1.0 inch in width
  1.0 inch in length and 2.5 inches in width
  1.5 inches in length and 3.0 inches in width
  0.75 inches in length and 3.0 inches in width
  $^{11}/_{16}$ inches in length and 2.5 inches in width
  1.25 inches in length and 2.0 inches in width In other representative embodiments, an adhesive element 180 can have these dimensions:
  2.25 inches in length and 0.75 inches in width; or
  2.25 inches in width and 0.75 inches in length In other representative embodiments, an adhesive element 180 can have these dimensions:
  2.0 inches in length and $^9/_{16}$ inches in width; or
  2.0 inches in width and $^9/_{16}$ inches in length In still another representative embodiment, an adhesive element 180 can have any dimensions that fall within the following ranges:
  (i) greater than 0.0000000001 inches and less than ten inches in length, and
  (ii) greater than 0.0000000001 inches and less than ten inches in width.

In still another representative embodiment, an adhesive element 180 can have any dimensions that fall within the following ranges:
(i) greater than 0.0000000001 inches and less than eight inches in length, and
(ii) greater than 0.0000000001 inches and less than eight inches in width.

In still another representative embodiment, an adhesive element 180 can have any dimensions that fall within the following ranges:
(i) greater than 0.0000000001 inches and less than six inches in length, and
(ii) greater than 0.0000000001 inches and less than six inches in width.

In still another representative embodiment, an adhesive element 180 can have any dimensions that fall within the following ranges:
(i) greater than 0.00000001 inches and less than six inches in length, and
(ii) greater than 0.00000001 inches and less than six inches in width.

In still another representative embodiment, an adhesive element 180 can have any dimensions that fall within the following ranges:
(i) greater than 0.00000001 inches and less than three inches in length, and
(ii) greater than 0.00000001 inches and less than three inches in width.

In still another representative embodiment, an adhesive element 180 can have any dimensions that fall within the following ranges:
(i) greater than 0.001 inches and less than three inches in length, and
(ii) greater than 0.001 inches and less than three inches in width.

In yet another representative embodiment, an adhesive element 180 can have an overall surface area that is greater than 0.001 square inches and less than 1,000 square inches. The "overall surface area" is defined as the total sum of all the areas of all the sides of the adhesive element 180.

In yet another representative embodiment, an adhesive element 180 can have an overall surface area that is greater than 0.001 square inches and less than 900 square inches.

In yet another representative embodiment, an adhesive element 180 can have an overall surface area that is greater than 0.001 square inches and less than 800 square inches.

In yet another representative embodiment, an adhesive element 180 can have an overall surface area that is greater than 0.001 square inches and less than 700 square inches.

In yet another representative embodiment, an adhesive element 180 can have an overall surface area that is greater than 0.001 square inches and less than 600 square inches.

In yet another representative embodiment, an adhesive element 180 can have an overall surface area that is greater than 0.001 square inches and less than 500 square inches.

In yet another representative embodiment, an adhesive element 180 can have an overall surface area that is greater than 0.001 square inches and less than 400 square inches.

In yet another representative embodiment, an adhesive element 180 can have an overall surface area that is greater than 0.001 square inches and less than 300 square inches.

In yet another representative embodiment, an adhesive element 180 can have an overall surface area that is greater than 0.001 square inches and less than 200 square inches.

In yet another representative embodiment, an adhesive element 180 can have an overall surface area that is greater than 0.001 square inches and less than 100 square inches.

These non-limiting examples, described above, do not limit the scope of the invention in any way, and it is to be understood that a generally rectangular adhesive element 180 may have any other dimensions as needed or desired.

Representative T-Shaped Adhesive Element

According to another preferred embodiment, the present invention contemplates a secure tampon which comprises an absorbent object 110 which is securely attached to at least one or more connector elements 140, and further wherein the one or more connector elements 140 are, in turn, safely and securely attached to at least one or more T-shaped adhesive elements 280. One example of a representative T-shaped adhesive element 280 is described in more detail below, with reference to FIGS. 7A and 7B.

Figure 7A:
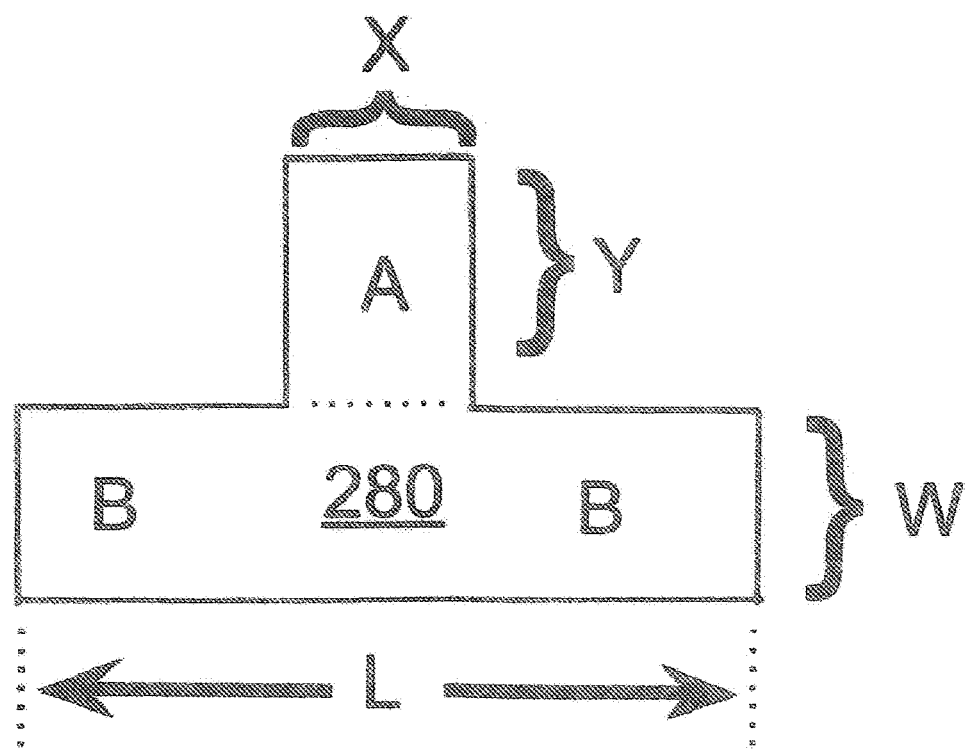
FIG. 7A depicts another preferred embodiment that shows a front side of a T-shape adhesive element.

Referring to FIG. 7A, the T-shaped adhesive element 280 has, on a front side, an upper square-shaped portion (labeled "A") and a lower rectangular portion (labeled "B"). In addition, referring to FIG. 7B, the T-shaped adhesive element 280 also has, on the other side (or back side), an upper square-shaped portion 285 (see area labeled "AA") and a lower rectangular-shaped portion 287 (see area labeled "BB").

Figure 7B:
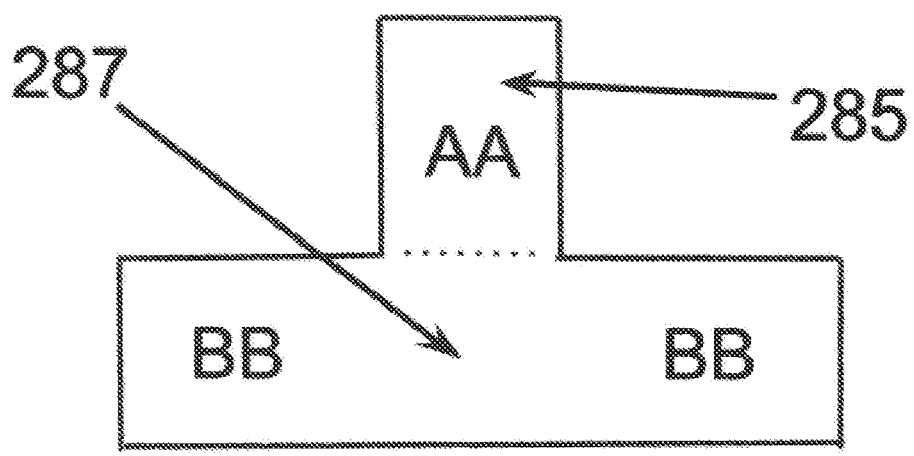
FIG. 7B depicts another preferred embodiment that shows a back side of a T-shape adhesive element.

Referring again to FIG. 7A, in one preferred embodiment, the lower rectangular-shaped portion of the adhesive element 280 has double-sided tape that includes peel-off adhesive strips on both sides, i.e., on both (i) the front side "B" of the lower rectangular-shaped portion of the adhesive element 280 as shown in FIG. 7A, and also (ii) on the back side "BB" of the lower rectangular-shaped portion 287 of the adhesive element 280 as shown in FIG. 7B.

In a different embodiment, the upper square-shaped portion of the T-shaped adhesive element 280 has double-sided tape that includes peel off adhesive strips on both sides, i.e., on both (i) the front side "A" of the upper square-shaped portion of the adhesive element 280 as shown in FIG. 7A, and also (ii) on the back side "AA" of the upper square-shaped portion 285 of the adhesive element 280 as shown in FIG. 7B.

In still yet another preferred embodiment, the adhesive element 280 has double-sided tape, and more specifically peel-off adhesive strips on both the upper and lower areas on both sides of the adhesive element 280, so that there are peel-off adhesive strips on these areas:
(i) on the front side "B" of the lower rectangular-shaped portion of the adhesive element 280 as shown in FIG. 7A;
(ii) on the back side "BB" of the lower rectangular-shaped portion 287 of the adhesive element 280 as shown in FIG. 7B;
(iii) on the front side "A" of the upper square-shaped portion of the adhesive element 280 as shown in FIG. 7A; and
(iv) on the back side "AA" of the upper square-shaped portion 285 of the adhesive element 280 as shown in FIG. 7B.

It has been surprisingly found that the use of the double-sided tape, with the peel-off adhesive strips, has significant advantages including significantly improving the ability of the adhesive element 280 to remain safely and securely adhered to the skin of the user as they are using the adhesive element 280.

In another representative embodiment, when multiple connector elements 140 are used, it is contemplated that there can be multiple points of contact to an adhesive element 180, 280 or 380. More specifically, it is contemplated (when multiple connector elements 140 are used) that each separate end of each separate connector element 140 is safely and securely connected to distinct sites (distinct points of contact) on an adhesive element, including adhesive element 180, 280 or 380 as described herein. These multiple points of contact have been surprisingly found to add significant strength and durability for keeping a tampon safely and securely in place (including the secure tampons described herein, in accordance with the present invention) when a female user is using the tampon in accordance with the present invention.

In addition, it is contemplated that sterile manufacturing and sterile packaging can be utilized in the manufacturing, production and packaging of the tampons described herein and contemplated within the present invention.

Moreover, the present invention also contemplates the use of a desiccant or hygroscopic agent, and optionally the use of one or more antioxidants, during manufacturing and packaging to reduce moisture content and also to protect a tampon from unwanted oxidative damage.

In yet another embodiment, the upper square-shaped portion is manufactured so that it has an adhesive peel strip (e.g., an adhesive layer) on only one side.

In yet another embodiment, the lower rectangular-shaped portion is manufactured so that it has an adhesive peel-off strip (e.g., an adhesive layer) on only one side.

Referring again to FIG. 7A, the upper square-shaped portion (labeled "A") of the adhesive element 280 has a length "X" which is measured as the total distance along the upper horizontal edge of the upper square-shaped portion. Also, as shown in FIG. 7A, the upper square-shaped portion of the adhesive element 280 has a width "Y" which is measured as the total distance along the vertical edge of the upper square-shaped portion. The T-shaped adhesive element 280 can be manufactured to have any desired dimensions of X and Y. In a preferred embodiment, the length "X" is about 0.5 inches (or ½ of an inch), and the width "Y" is about 0.5 inches (or ½ of an inch). In yet another preferred embodiment, the length "X" is about 0.75 inches (or ¾ of an inch), and the width "Y" is about 0.75 inches (or ¾ of an inch). In still yet another preferred embodiment, the length "X" is about one (1.0) inch, and the width "Y" is about one (1.0) inch.

Referring again to FIG. 7A, the lower rectangular portion of the adhesive element 280 has a length "L" which is measured as the total distance along the bottom horizontal edge of the adhesive element 280 (this distance along the bottom horizontal edge is measured as the length "L" between the two vertical dotted lines shown in FIG. 7A; each arrow in FIG. 7A points to one of the two vertical dotted lines). Also, as shown in FIG. 7A, the lower rectangular portion of the adhesive element 280 has a width "W" which is measured as the total distance along the vertical edge of the lower rectangular portion as clearly depicted in FIG. 7A. In a preferred embodiment, the lower rectangular portion has double-sided tape with peel off strips on both sides, i.e., on both the front side "B" of the lower rectangular portion shown in FIG. 7A, and also on the back side "BB" of the lower rectangular portion 287 shown in FIG. 7B. In another embodiment, the lower rectangular portion has a peel-off layer on the back side "BB" of the lower rectangular portion 287, but it is not double sided. In a preferred embodiment, the lower rectangular portion of the adhesive element 280 has a width "W" of about 0.5 inches (½ inches) and a length "L" of about 2.0 inches (two inches). In another preferred embodiment, the lower rectangular portion of the adhesive element 280 has a width "W" of about 0.75 inches (¾ inches) and a length "L" of about 2.25 inches (two and one-quarter inches). In yet another preferred embodiment, the lower rectangular portion of the adhesive element 280 has a width "W" of about one (1.0) inch and a length "L" of about 2.50 inches (two and one-half inches). However, the embodiments can be any size or shape that both secures the tampon to the woman's body preferably for eight (8) hours, despite activities such as swimming, showering, running and simply sitting and also enables ease of both adhesion and removal of the adhesive element by the woman.

In a preferred embodiment, the adhesive elements 180 and 280 can be tan, white or another color, and can be made of polyurethane and/or polyolefin materials, using woven or nonwoven materials. In another embodiment, the adhesive elements 180 and 280 can be made of a polyester spunlace nonwoven tape. In yet another embodiment, the adhesive elements 180 and 280 can be made of an acrylate adhesive material. In yet another embodiment, the adhesive elements 180 and 280 can also include a liner made of poly-coated paper, and can optionally include a silicone release material.

In still yet another embodiment, the adhesive elements 180 and 280 can be made of any hypoallergenic material such as, for example, 3M-brand (3M™) nonwoven medical tape (including, but not limited to, 3M-brand (3M™) Product Number 9907T and 3M-brand (3M™) Product Number 9916.

Additional Representative Embodiments of the Present Invention

Additional representative embodiments of the present invention are described below. These representative embodiments are for illustration purposes only, and do not limit the scope of the invention in any way.

Figure 8:
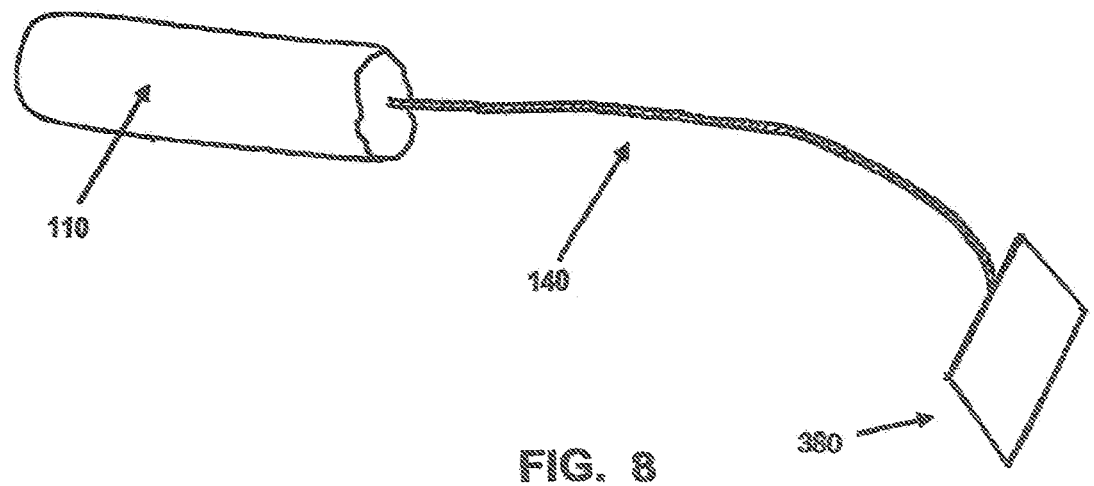
FIG. 8 depicts another preferred embodiment of a secure tampon of the present invention, in which a connector element is safely and securely attached to another type of adhesive element 380.

Referring to FIG. 8, another preferred embodiment of a secure tampon of the present invention is shown in which a connector element is safely and securely attached to another type of adhesive element 380.

It is to be understood that the term "adhesive element 380", as used throughout this description of the present invention, and as shown schematically in the figures, is intended to broadly refer to any type of safe and effective adhesive substance or adhesive mechanism that can be used to safely and securely keep the secure tampon of the present invention in place, when a woman is using the secure tampon, such that the secure tampon will not get lost when the woman is using it. Some representative, non-limiting examples of an adhesive element 380 include, but are not limited to, an adhesive element that comprises one or more sticker, safe removable glue, safe body paint that peels off, or a combination thereof.

Referring again to FIG. 8, a secure tampon comprises an absorbent object 110 (the absorbent object 110 is shown on the left side of FIG. 8) which is securely attached to at least one or more connector elements 140 (a connector element can include, for example, a single cord, a single string, or more than one cord or string), and further wherein the one or more connector elements 140 are, in turn, safely and securely attached to at least one or more adhesive elements 380 (for illustration purposes only, only one adhesive element 380 is shown on the right side of FIG. 8). In a preferred embodiment, the adhesive element 380 is a sticker. In other embodiments, it is to be understood that more than one adhesive element 380 can also be used when there are more than one connector elements 140. The one or more adhesive elements 380 (as shown in FIG. 8) comfortably, securely and safely attach to at least one area of the tampon wearer's body. The tampon wearer can safely remove the one or more adhesive elements 380 at any time.

Figure 9:
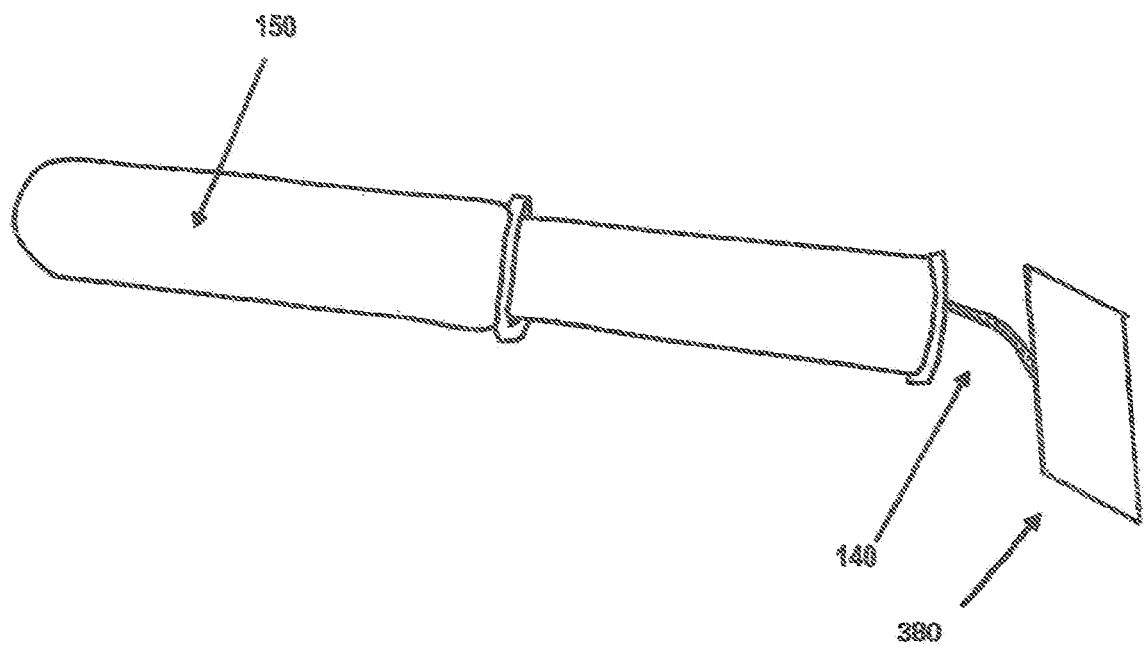
FIG. 9 depicts yet another preferred embodiment that shows a secure tampon with an applicator 150, and a connector element that is safely and securely attached to another type of adhesive element 380.

Referring to FIG. 9, yet another preferred embodiment is shown depicting a secure tampon with an applicator 150, and a connector element 140 that is safely and securely attached to adhesive element 380. Many women may prefer to use a secure tampon with an applicator 150. Any suitable applicator can be used to safely place the secure tampon. In a preferred embodiment, the present invention includes the absorbent object 110 (see FIG. 8) that a woman inserts into her vagina, and an applicator 150 (for example, a plastic applicator) (e.g., as shown in FIG. 9) that the woman uses to insert the absorbent object 110 in her vagina. In one example, the woman places the absorbent object 110 in her vagina. One such example of a secure tampon 100 with an applicator 150, in accordance with the present invention, is shown in FIG. 9.

Figure 10:
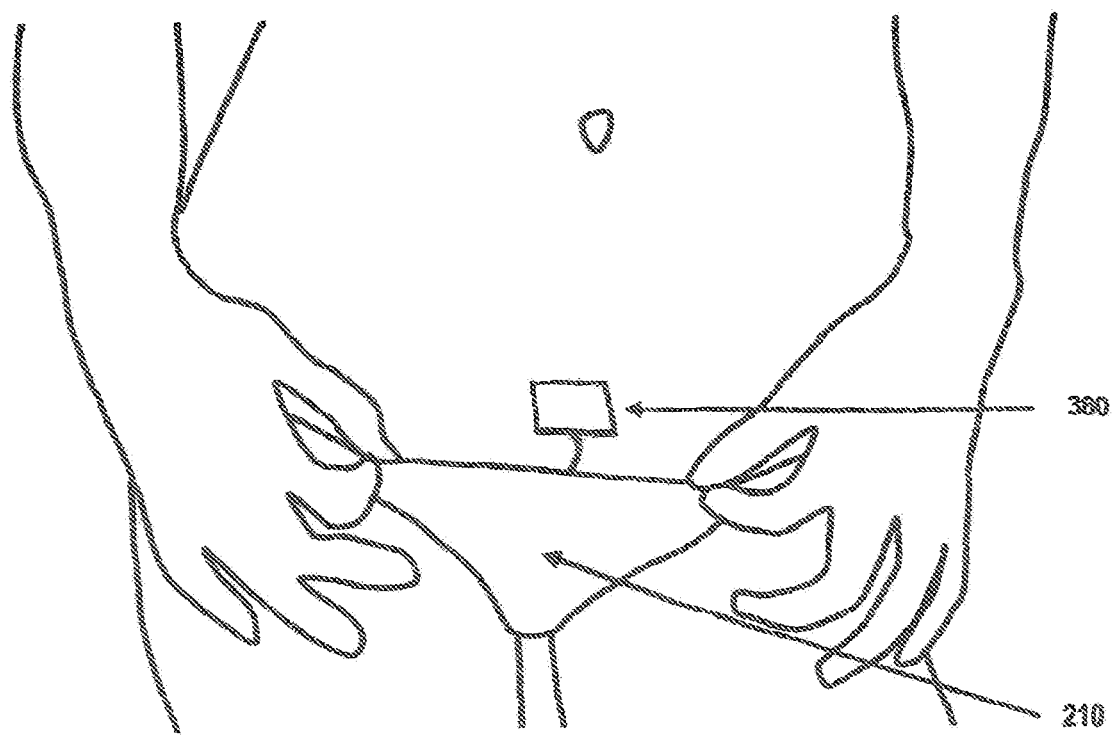
FIG. 10 depicts another preferred embodiment that shows a representative close-up view of the mid-region of a woman wearing underwear after applying a secure tampon of the present invention, and which also depicts adhesive element 380.

FIG. 10 depicts another preferred embodiment that shows a representative close-up view of the mid-region of a woman wearing underwear after applying a secure tampon of the present invention, and which also depicts adhesive element 380. As shown in FIG. 10, the woman has safely and securely adhered the adhesive element 380 to the skin of her pubic region. This is shown, by way of example, by the sticker (one example of an adhesive element 380) that the woman has adhered to her skin, as shown in FIG. 10. An adhesive element 380, such as a sticker or safe body paint that peels off, can also have any aesthetic design (comprising one or more different shapes and/or colors in the design and the ability to change color). The woman can safely remove the adhesive element 380 at any time.

As shown in FIG. 10, the adhesive element 380 secures the tampon to a woman's body, and she therefore also sees the adhesive element 380 and she will not forget about it or lose the string (or other connective element) inside her. As described herein, the secure tampon of the present invention also offers improved hygiene because the string will not get lost near the behind, possibly minimizing *E. coli* bacterial infections.

Figure 11:
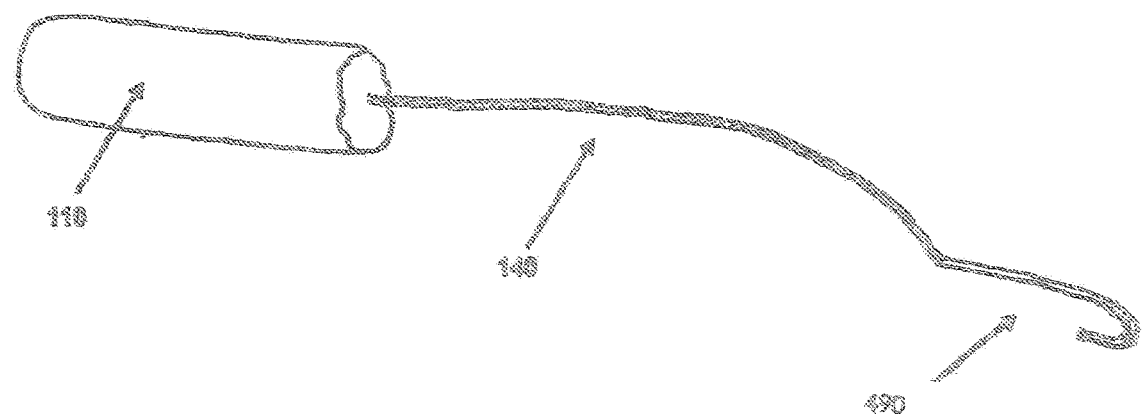
FIG. 11 depicts another preferred embodiment of a secure tampon 100 according to the present invention, in which a connector element is safely and securely attached to a fastening element 490.

FIG. 11 depicts another preferred embodiment of a secure tampon 100 according to the present invention, in which a connector element is safely and securely attached to a fastening element 490.

It is to be understood that the term "fastening element" (for example a fastening element 490) as used throughout this description of the present invention, is intended to broadly refer to any safe and effective component, device, product, mechanism, apparatus or other physical, tangible object that functions to safely and securely fasten, attach or secure the one or more connector elements 140 to an undergarment being worn by a user of the secure tampon of the invention. An undergarment can include, for example, underwear being worn by a woman, while the woman is also using the secure tampon of the present invention. Some non-limiting examples of such a fastening element include, but are not limited to, any type of hook or hook-shaped element, clasp or clasping element, or other safe and effective component, device, product, mechanism, apparatus or other physical, tangible object that functions to safely and securely fasten, attach or secure the one or more connector elements 140 to an undergarment being worn by a user of the secure tampon of the invention.

One non-limiting example of a fastening element 490, as shown in FIG. 11 (and also shown in FIGS. 12, 13 and 14), is a hook or hook-shaped element. When a hook or hook-shaped element is used in accordance with the present invention (further description of such a hook or hook-shaped element is described herein), there are several surprising and unexpected advantages. For example, a hook or hook-shaped element can be hooked or clasped over a woman's underwear in order to keep a tampon of the present invention safely and securely in place when the woman is using the tampon. It is also contemplated that the hook or hook-shaped element can easily be unhooked if needed or desired, for instance when the woman goes to use the restroom. Once the woman has finished using the restroom, she can then easily re hook the hook or hook-shaped element afterwards.

The hook or hook-shaped element has other benefits. For example, if a woman or tampon wearer is allergic to tape or does not like to use tape, or if the woman or tampon wearer has pubic hair and is afraid of tape on the pubic hair, then the hook or hook-shaped element can be a better option.

In another embodiment, a soft material (such as, for example, a soft cap made of a safe and non-toxic material) can be placed over the hook or hook-shaped element, so that the hook or hook-shaped element does not injure the skin of the user when it is being used.

In one embodiment, when a woman is using the secure tampon of the present invention, the one or more connector elements 140 are securely attached to the fastening element 490 (which, as shown in FIGS. 11, 12, 13 and 14, is a hook-shaped element). The hook-shaped element securely fits over the edge of the woman's undergarment (for example, her underwear) and in this manner, the secure tampon of the invention will remain securely in place and will not get lost. A hook or hook-shaped element may be curved or have any desired shape or angle, as long as it functions to safely and securely fasten, attach or secure the one or more connector elements 140 to an undergarment being worn by a user of the secure tampon of the invention. Although not shown in the figures, one preferred embodiment is to include a soft protective cap over the hook or hook-shaped element. In this manner, the soft protective cap is very effective for protecting the user from injury by the hook or hook-shaped element, such that the hook or hook-shaped element does not damage, hook or injure the user's skin when it is being used.

Figure 12:
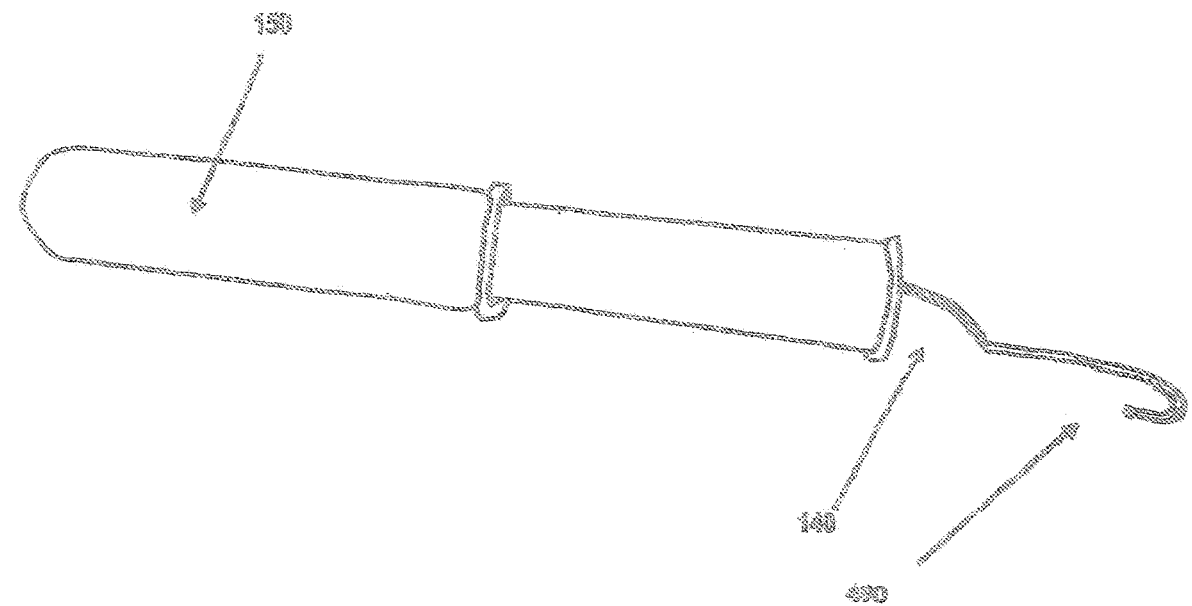
FIG. 12 depicts yet another preferred embodiment that shows a secure tampon with an applicator 150, and a connector element that is safely and securely attached to a fastening element 490.

FIG. 12 depicts yet another preferred embodiment that shows a secure tampon with an applicator 150, and a connector element that is safely and securely attached to a fastening element 490 (which, as depicted in this example, is a hook-shaped element).

Figure 13:
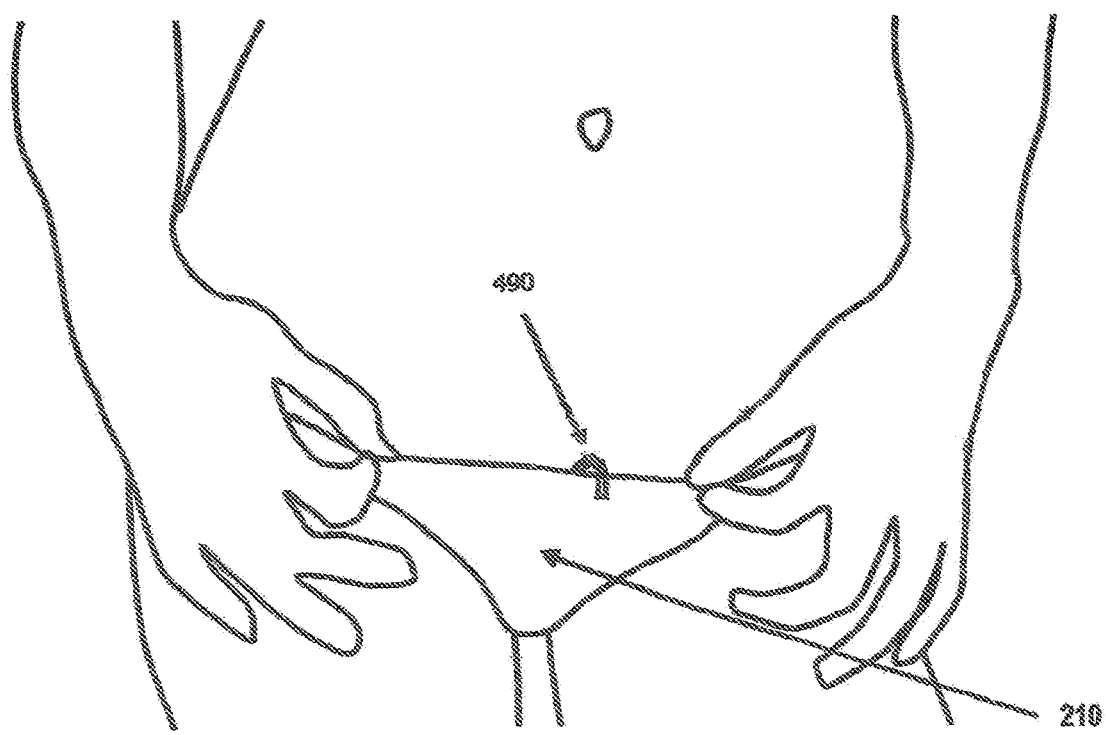
FIG. 13 depicts yet another preferred embodiment that shows a representative close-up view of the mid-region of a woman wearing underwear after applying a secure tampon of the present invention, and this figure also depicts a fastening element 490.

FIG. 13 depicts yet another preferred embodiment that shows a representative close-up view of the mid-region of a woman wearing underwear after applying a secure tampon of the present invention, and this figure also depicts a fastening element 490 (which, as depicted in this example, is a hook-shaped element).

Figure 14:
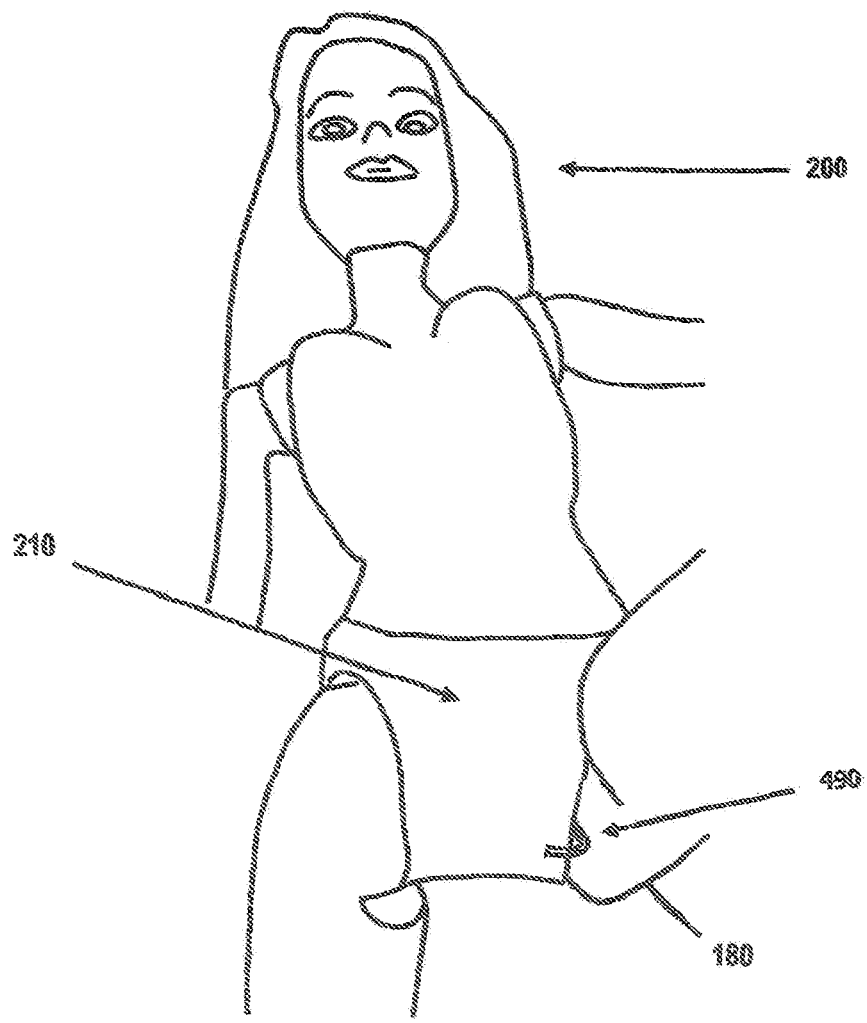
FIG. 14 depicts another embodiment of a woman wearing underwear after application of a secure tampon of the invention, and this figure also depicts a fastening element 490.

FIG. 14 depicts another embodiment of a woman wearing underwear after application of a secure tampon of the invention, and this figure also depicts a fastening element 490 (which, as depicted in this example, is a hook-shaped element).

Other Representative Embodiments

Other representative embodiments of the invention are described herein, and it is to be understood that these representative embodiments do not limit the scope of the invention in any way.

Representative Method of Using a Tape Dispenser to Obtain One or More Adhesive Elements for Use in Accordance with the Present Invention The present invention also contemplates, in another embodiment, that a tape dispenser can conveniently, easily and reliably be used by a user (e.g., a woman) to obtain one or more adhesive elements for use in accordance with the present invention, i.e., for use in safely securing a tampon in place when the tampon is used by the woman as described herein.

Figure 15A:
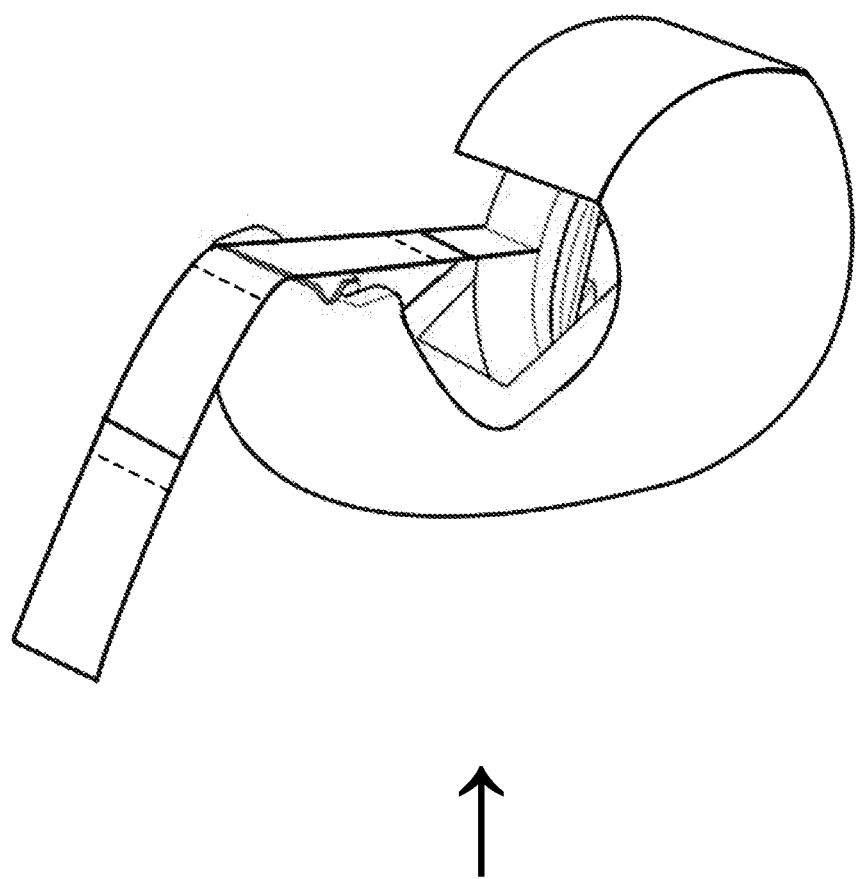
FIG. 15A depicts one example of a tape dispenser that can be used for obtaining adhesive elements from a perforated roll of adhesive material.

FIG. 15A depicts one example of a tape dispenser 510 that can be used for obtaining adhesive elements from a perforated roll of adhesive material.

The tape dispenser 510 can be any size, shape and color and have any dimensions. The present invention also contemplates that the tape dispenser 510 can be made of any safe material for consumer use and can, for example, be a medical grade tape dispenser.

Figure 15B:
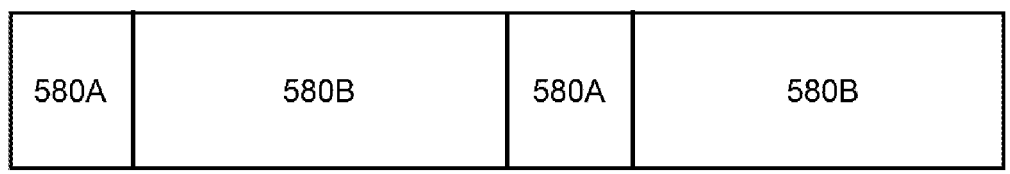
FIG. 15B depicts representative examples of adhesive elements of different sizes that can be used in accordance with the present invention.
Figure 15B:
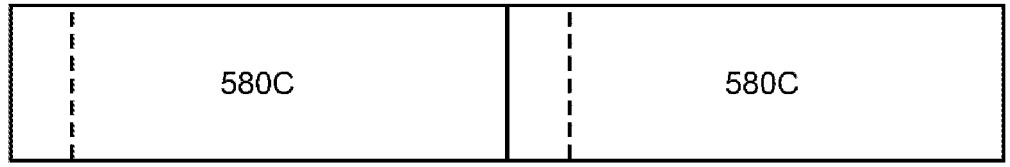

In a preferred embodiment, as shown in FIG. 15B, one section of a roll of adhesive material is shown, and this one section of a roll of adhesive material includes a number of adhesive elements of different sizes. As shown in FIG. 15B, (i) each adhesive element 580A is one size and (ii) each adhesive element 580B is larger in size, e.g., because of a greater width of each adhesive element 580B, compared to the relatively smaller width of each adhesive element 580A. In one embodiment, each adhesive element 580B is approximately three times greater in width compared to the width of each adhesive element 580A.

In one embodiment, adhesive elements 580A and 580B have the following dimensions:

Each adhesive element 580A: 2.25 inches×0.75 inches (with respective small bottom/back piece being 0.75 inches× 0.75 inches)

Each adhesive element 580B: 2.0 inches×9/16 inches (with respective small bottom/back piece being 9/16 inches×9/16 inches)

In a preferred embodiment, the size of adhesive element 580A is different from the size of adhesive element 580B.

Adhesive elements 580A and 580B can be the same color or different colors.

Adhesive elements 580A and 580B can also have any size that is described herein for adhesive element 180.

Adhesive elements 580A and 580B can also have any overall surface area that is described herein for adhesive element 180.

In another embodiment, the size of adhesive element 580A is the same as the size of adhesive element 580B.

According to one example, a user (e.g., a woman) can remove one or more of adhesive elements 580A and 580B from a roll of adhesive material by carefully removing or separating each separate adhesive element along perforations in the roll of adhesive material as shown in FIG. 15B. The perforations in the roll of adhesive material make it easy to determine where to cut each separate adhesive element in order to separate each separate adhesive element.

FIG. 15B also shows adhesive element 580C according to one embodiment. As shown in FIG. 15B, adhesive element 580C is an example of two adhesive elements on a tape dispenser. The dotted line shows where each adhesive element will be folded around a string or other connector element.

Figure 16A:
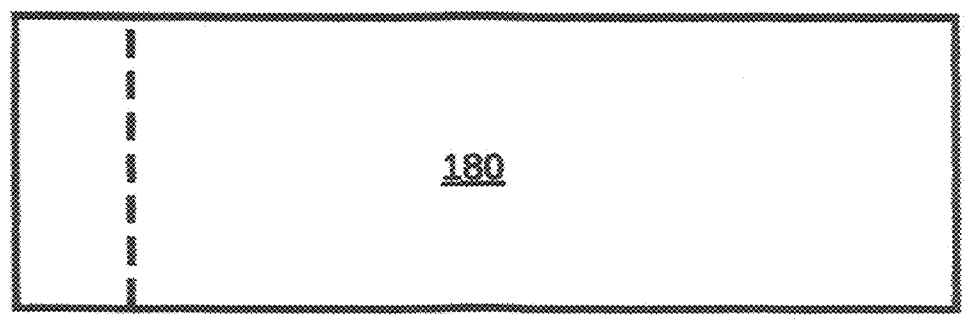
FIG. 16A depicts an adhesive element that is unfolded with no string (i.e. no connector element) in place.

FIG. 16A depicts an adhesive element that is unfolded with no string (i.e. no connector element) in place.

Figure 16B:
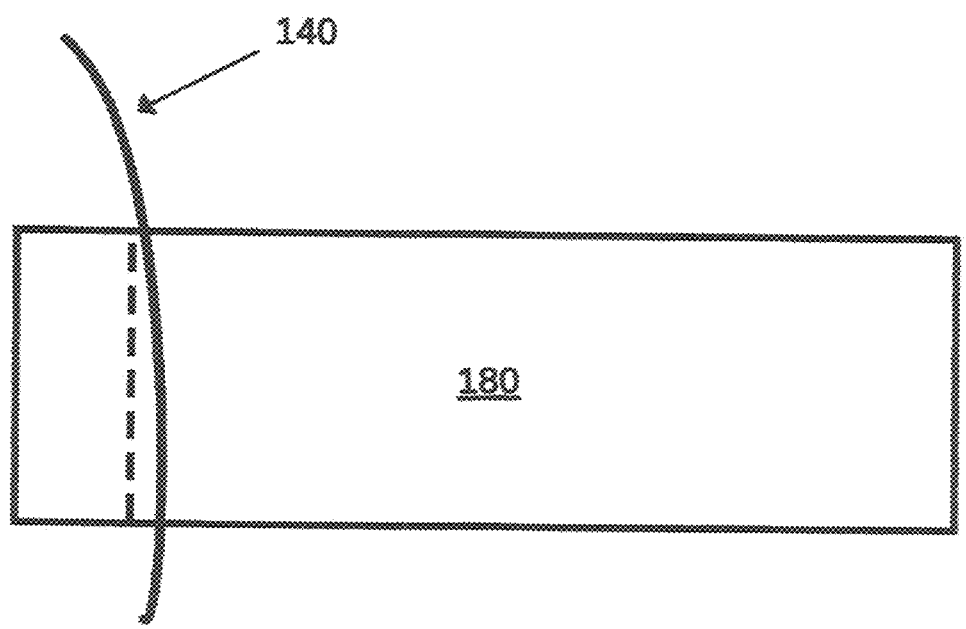
FIG. 16B depicts an adhesive element that is unfolded with a string (i.e. with a connector element) in place.

FIG. 16B depicts an adhesive element that is unfolded with a string (i.e. with a connector element) in place.

Figure 16C:
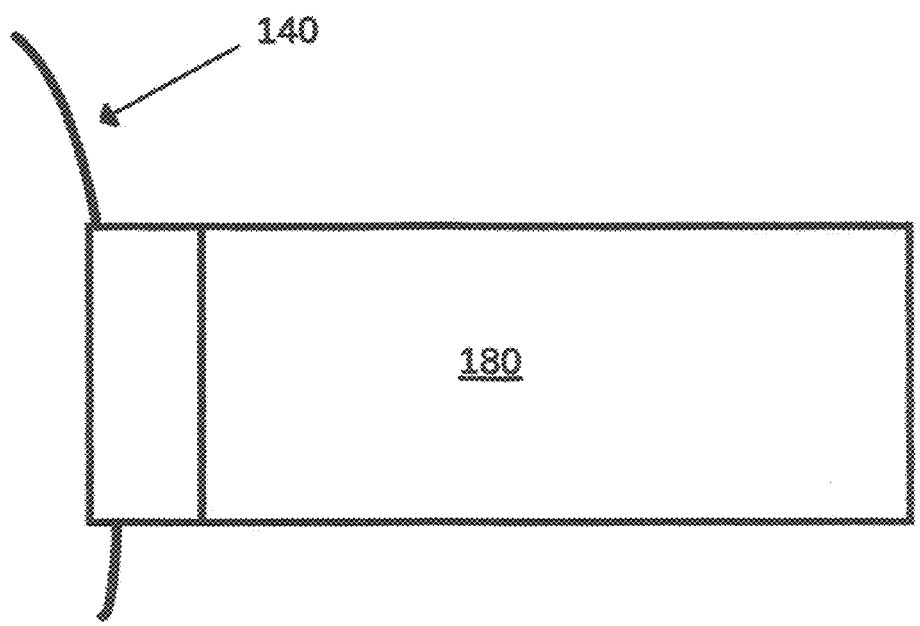
FIG. 16C depicts an adhesive element that is folded with a string (i.e. with a connector element) in place.

FIG. 16C depicts an adhesive element that is folded with a string (i.e. with a connector element) in place.

Figure 17A:
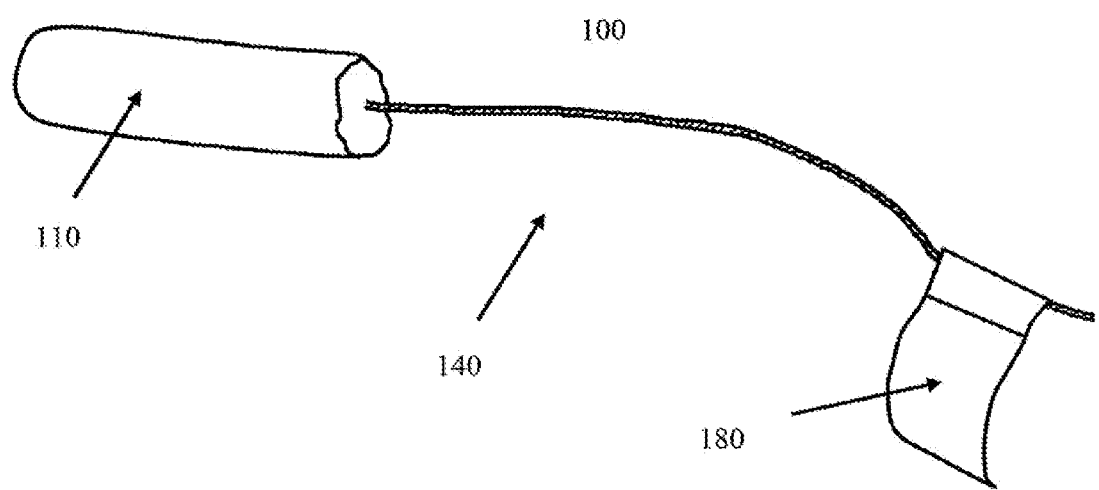
FIG. 17A depicts another embodiment of a secure tampon 100 according to the present invention, in which an adhesive element is securely folded around a string.

FIG. 17A depicts another embodiment of a secure tampon 100 according to the present invention, in which an adhesive element is securely folded around a string.

Figure 17B:
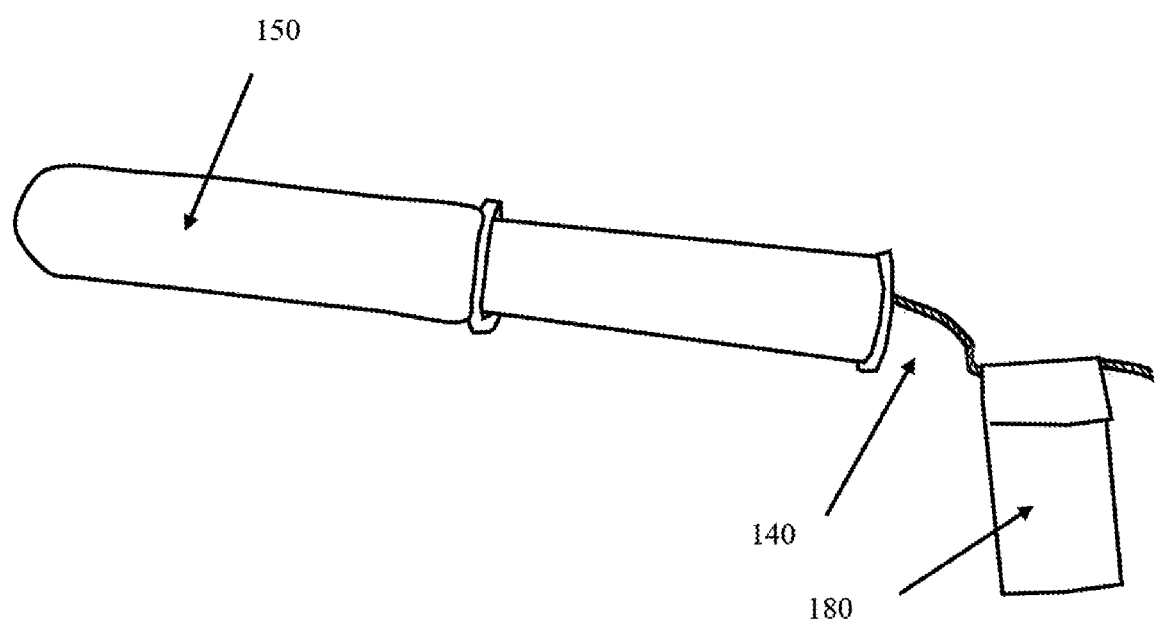
FIG. 17B depicts another embodiment of a secure tampon with an applicator 150, in which an adhesive element is securely folded around a string.

FIG. 17B depicts another embodiment of a secure tampon with an applicator 150, in which an adhesive element is securely folded around a string.

In one embodiment, a woman can, for example, keep a tampon securely in place by securely attaching the adhesive elements to one or more connector elements and then also securely adhering each of the adhesive elements to the woman's body in order to keep the tampon securely in place, in accordance with the present invention as described herein. The roll of adhesive material can be made from any suitable adhesive material, including but not limited to micropore hypoallergenic paper surgical tape. It is to be understood that this is a non-limiting example and does not limit the scope of the invention in any way.

Representative Manufacturing of the Secure Tampons of the Present Invention

The present invention contemplates preferred methods of manufacturing the secure tampons of the present invention. In preferred methods, the secure tampons of the present invention are preferably manufactured by a process in which each absorbent object is first securely attached to a connector element (for instance, each absorbent object is securely attached to a string). In some embodiments, each absorbent object can be securely attached to one or more connector elements.

The present invention also contemplates that each absorbent object can optionally be placed in an applicator.

In preferred methods of manufacturing the secure tampons of the present invention, in which each absorbent object is placed in an applicator, the following additional steps are performed:

1. Each absorbent object, securely attached to a connector element, is then rolled down a conveyor belt horizontally, or in a generally horizontal manner;
2. Each string or connector element, securely attached to each absorbent object, is then stamped with adhesive element (as described herein, in accordance with the present invention) on both sides of the string or connector element, such that the adhesive element adheres to both sides of the tampon string or connector element; and then
3. The adhesive element is rolled up and pushed into the applicator.

In another embodiment, after each absorbent object with a string or connector element is created but not yet inserted into an applicator, a manufacturing process can be utilized to perform the following steps:

1. The tampon string or connector element, securely attached to each absorbent object,) is stamped with adhesive element (as described herein, in accordance with the present invention) on both sides of the string or connector element, such that the adhesive element adheres to both sides of the tampon string or connector element;
2. Then each tampon is inserted into an applicator; and then
3. The adhesive element is rolled up and pushed into the applicator.

In certain embodiments, as depicted in FIGS. 17A and 17B, the present invention also contemplates that connector element 140 (for example, a string) can be securely attached at one end of an adhesive element 180 (or, in other embodiments, adhesive element 280 or 380) in such a manner that the "end" or "flap" of the adhesive element 180 can be securely folded over the end of the connector element 140.

In other embodiments, one or more connector elements 140 can be securely attached to any other area or region of an adhesive element 180.

The present invention also contemplates that any manufacturing equipment and any manufacturing process can be used, even on an industrial scale, for example with industrial tape dispensers and rolls of adhesive material to produce adhesive elements on a larger scale and to manufacture the secure tampons for use in accordance with the present invention.

In one representative, non-limiting example of a manufacturing process, an optional step in the manufacturing process is to produce an absorbent object that includes fiber integrated nonwoven material. This optional step in the manufacturing process is described in more detail below.

Optional Step in a Manufacturing Process: Producing an Absorbent Object that Includes Fiber Integrated Nonwoven Material In a preferred non-limiting embodiment, the secure tampons of the present invention can generally be manufactured by manufacturing techniques as described herein. In a preferred embodiment, a first optional step in manufacturing the secure tampons of the present invention involves forming an absorbent object (for example, absorbent object 110) from a mass of absorbent material and further using, for example, needle punching or spunlacing as described herein to produce an absorbent object that includes fiber integrated nonwoven material. The mass of absorbent material is generally in the form of one or more layers of fibrous materials. In a preferred embodiment, the absorbent object (for example, absorbent object 110) preferably comprises fiber integrated nonwoven material. Fiber integration of nonwoven material can occur via any desired or suitable process, for example which entangles fibers in a Z-direction (either positive or negative). The term "pledget" is also used herein to refer to a small amount of absorbent material, absorbent cotton or other soft absorbent material. Preferably, the absorbent material should have sufficient Z-direction integration of the fibers along the length of the pledget to provide desired and efficient absorption of fluids when the secure tampons of the present invention are being used by a user. Examples of processes which can be used for the fiber integration include, for instance, but are not limited to, needle punching or spunlacing.

In one embodiment, needle punching can be utilized and involves, for example, mechanical interlocking of fibers from a spunbonded web. With a needle punching process, for example, a plurality of barbed needles can repeatedly pass in and out of a nonwoven web and push fibers of the nonwoven web in a positive and/or negative Z-direction. For needle punching, the present invention contemplates the use of certain equipment to produce a spunbonded web of fibers. For example, bale openers, a mixer, carding machines, a preneedler and a needle loom can be used. The present invention contemplates formation of nonwoven webs prior to needle punching. For the needle punching any preneedler can be used, for example a Truzschler ENL-01 preneedler, ID #364600, 5000 needles per meter, 15×16×36×3.5 M222 G 53017 needles available from Trutzschler. Also, any needle loom can be used, for example the needle loom can be an Asselin Model A50RL, series 1189, 7000 needles per meter, with 15×32×40×3.5 R222 G530P7 needles available from Andritz. In one example, a needlepunched absorbent object has a fiber blend ratio of 75 percent Galaxy™ rayon and 25 percent cotton. Other needlepunched absorbent objects can have any desired fiber blend ratio of different materials.

In another embodiment, a spunlacing process can be used preferably using high-speed jets of water to cause interlocking of fibers of a nonwoven web. The high-speed jets of water preferably push fibers of the nonwoven web in the positive or negative Z-direction. For spunlacing, any other suitable equipment can be used for producing the interlocking of fibers of a nonwoven web. For example, bale openers and carding machines can be used for the spunlacing process. For the spunlacing operation, an Aqua-Jet spunlace system from Fleissner, a dryer from Trutzschler, a drum dryer from Fleissner, and a winder from Menzel can be utilized. The number of jet heads can be varied as desired or needed and, for example, having a plurality of holes each having a diameter of 120 microns (120 μm) and the number of holes being 40 holes per inch. For the spunlacing process, any suitable pressure can be used including, for example, pressures of 20, 40, or 50 bar.

As described herein, in some embodiments of the present invention, the absorbent object (such as, for example, absorbent object 110) preferably comprises fiber integrated nonwoven material. Preferably, the absorbent object should have sufficient integration of the fibers to absorb fluids during use in accordance with the present invention. In a preferred non-limiting embodiment, the secure tampons of the present invention are preferably manufactured using an absorbent object which has been compressed in any or all of the width direction, the radial direction, and the axial direction, in order to provide a tampon which is of a size and stability to allow insertion within the vagina or other body cavity. The secure tampons of the present invention can also be "fluid-expanding" tampons that expand or uncompress upon contact and absorption of fluid.

Placing the Manufactured Tampon Inside a Wrapper

In a preferred embodiment, after the steps described above have been performed for manufacturing the secure tampons of the present invention, further steps can optionally be performed to place each tampon inside a wrapper. A wrapper can have any size, shape, color or colors, dimensions, thickness, and can be made of any wrapper material or combination of wrapper materials. The wrapper can, for example, be made of any suitable plastic material. The size of the wrapper can vary as needed or desired. In one example, which does not limit the scope of the invention, a wrapper is about 1.5 inches×about 6.5 inches. By 'wrapper material' it is meant herein any material suitable to be used for hygienically wrapping tampons. A wrapper material preferably has two surfaces, including an 'inner surface' directed towards the wrapped tampon, and an 'outer surface' aligned opposite to the inner surface. Typically, suitable wrapper materials for use herein are flexible polymeric films, having a thickness of less than 1 mm. Examples for wrapper materials suitable for use are polymeric films made of polyethylene, polypropylene, polyester, cellophane, polyamide, poly(vinyl chloride), ethylene-vinyl acetate copolymer and the like. Alternatively, heat-shrinkable films, stretch films, pre-stretched elastic material, or combinations thereof may be used to create the wrapper. While not limited to a given composition, preferred compositions of heat-shrinkable and stretch films comprise primarily polyolefins such as polyethylene and polypropylene, or polyvinyl chloride. Polystyrene and polyethylene-terephthalate (PET), although being not heat sealable, are also suitable for use. Wrappers consisting of those materials can be closed by gluing with an adhesive.

These non-limiting examples, described above, do not limit the scope of the invention in any way, and it is to be understood that the present invention contemplates that other manufacturing methods may also be used.

Representative Use of "Digital Tampons"

In another embodiment of the present invention, a "digital tampon" can be used instead of an applicator tampon. The term "digital tampon" is intended to refer to a tampon with no applicator, or an applicator-free tampon. In one example, the following steps could be utilized in a very effective manner:
(i) a digital tampon is manufactured, wherein the digital tampon is securely connected to one end of a connector element (for example, a string or connector element 140);
(ii) an adhesive element (for example, a piece of adhesive tape or an adhesive element 180, 280 or 380) is added by securely attaching the adhesive element to the other end of the connector element (for example, the string or the connector element 140) as described herein in other embodiments of the invention;
(iii) then the adhesive element would be wrapped around the digital tampon and packaged for sale to a consumer.

In some embodiments, a digital tampon has the advantage of easy and reliable manufacturing, and a digital tampon can be more easily manufactured compared to an applicator tampon.

Use of One or More Different Therapeutic Agents

In yet other preferred embodiments of the present invention, one or more different therapeutic agents can be used (including, but not limited to, one or more safe, effective and approved anti-inflammatory agents, one or more cannabinoids, cannabidiol, antibiotic agents, anti-irritants, or any other suitable therapeutic agent, or any combination thereof). These one or more therapeutic agents can, for example, be included at appropriate, safe and effective amount(s) or concentration(s) in a suitable formulation within one or more adhesive elements (for example, adhesive elements 180, 280 or 380). Preferably, the adhesive elements can be manufactured in advance to contain the appropriate, safe and effective amount(s) or concentration(s) of one or more therapeutic agents in a suitable formulation. In addition to one or more therapeutic agents, a suitable formulation can also include one or more safe and approved excipients.

As described herein, at least one or more adhesive elements can be securely but temporarily attached to at least one area of the tampon wearer's body. Therefore, when an adhesive element is securely but temporarily attached to the tampon wearer's body, and when the same adhesive element contains appropriate, safe and effective amount(s) or concentration(s) of one or more therapeutic agents in a suitable formulation, then it is contemplated that the one or more therapeutic agents will be effective preferably via transdermal delivery in a totally safe and effective manner (i.e., delivery of the one or more agents in a totally safe and effective manner across the skin of the tampon wearer's body). Examples of suitable formulations for transdermal delivery include, but are not limited to, creams, oils, ointments, lotions and gels. In one embodiment, for transdermal delivery of one or more agents, an adhesive element can be manufactured in the form of a patch, wherein the patch is securely but temporarily attached to the tampon wearer's body for a desired or necessary period of time.

Preferably, the one or more therapeutic agents are effective in helping to safely and effectively reduce any possibility of itching, inflammation, infection and/or other possible condition or conditions when a woman is using the secure tampon of the present invention, and especially reducing any possibility of itching, inflammation, infection and/or other possible condition or conditions at the site where the one or more adhesive elements are in contact with the skin of the woman's body. This will significantly protect a female user when she wears one of the secure tampons of the present invention.

According to yet another embodiment, one or more therapeutic agents are effective in helping to safely and effectively reduce or eliminate any possibility of blood smell, lack of hygiene and other possible condition or conditions when a woman is using the secure tampon of the present invention. The one or more therapeutic agents are especially effective in reducing or eliminating any possibility of blood smell, lack of hygiene and/or other possible condition or conditions at the site where the one or more adhesive elements are in contact with the skin of the woman's body. This will significantly protect a female user when she wears one of the secure tampons of the present invention.

Use of One or More Different Scent Agents

In yet another preferred embodiment of the present invention, one or more different scent agents can be used (including, but not limited to, one or more safe, effective and approved essential oils, such as lavender, elderberry, tea tree oil, or any combination thereof). A "scent agent" is an agent that has, or produces, a nice or pleasant scent, smell or aroma. These one or more scent agents can, for example, be included at a safe and desired amount or concentration within one or more adhesive elements (for example, adhesive elements 180, 280 or 380). In one embodiment, one or more adhesive elements can be infused or permeated with a desired amount or concentration of one or more scent agents.

It is contemplated that a woman will desire to use a secure tampon of the present invention when one or more adhesive elements is infused or permeated with a desired amount or concentration of one or more scent agents. The scent agents will preferably have a nice fragrant aroma which should be nice and pleasant to a woman using a secure tampon of the present invention.

Any other type of scent agent (including, but not limited to, one or more safe, effective and approved essential oils) can be included at a safe and desired amount or concentration within one or more adhesive elements (for example, adhesive elements 180, 280 or 380). For example, other types of essential oils that can be used include, but are not limited to, basil essential oil, bergamot essential oil, mandarin essential oil, citronella essential oil, patchouli essential oil, lemon essential oil, fir essential oil, spearmint essential oil, lime essential oil, rosemary essential oil, tangerine essential oil, peppermint essential oil, lemongrass essential oil, sage essential oil, cedarwood essential oil, and/or eucalyptus essential oil.

In addition, the present invention contemplates the use of a combination or blend of one or more scent agents. In one embodiment, grapefruit-scented essential oil can be combined with any other essential oil to form a scented blend of oils.

Preferably, the adhesive elements can be manufactured in advance to contain an appropriate, safe and desired amount of one or more scent agents.

Representative Example of Use of a Secure Tampon of the Present Invention

1) A woman inserts an absorbent object into her vagina to absorb menstrual blood, wherein the absorbent object is securely attached to a string, and further wherein the string is, in turn, securely attached to at least one piece of pressure sensitive adhesive tape.
2) The woman peels off the back of the pressure sensitive adhesive tape.
3) The woman then places the pressure sensitive adhesive tape onto either her inner thigh or pubic bone, as close as possible to the vagina, but outside of it, such as on the labia majora or inner thigh.

4) When the woman is ready to remove the absorbent object, she simply just unpeels the pressure sensitive adhesive tape and removes the absorbent object out and discards it.

The foregoing descriptions of the embodiments of the present invention have been presented for purposes of illustration and description. They are not intended to be exhaustive or to limit the present invention to the precise forms disclosed. Although specific embodiments have been illustrated and described herein, other embodiments may be used without departing from the scope of the invention. This application is intended to cover any adaptations or variations of the embodiments discussed herein.

The invention claimed is:

1. A method of manufacturing a secure tampon, wherein the secure tampon comprises an absorbent object which is securely attached to at least one or more connector elements, and further wherein the one or more connector elements are safely and securely attached to at least one or more adhesive elements,
    wherein the method comprises using a tape dispenser to obtain the at least one or more adhesive elements from a perforated roll of adhesive material,
    wherein the at least one or more connector elements comprise a safe and non-toxic string, thread, filament, fiber, microfiber, yarn or other safe and non-toxic connective element,
    wherein the one or more adhesive elements have a shape that is generally round, circular, oval, elliptical, triangular, semicircle, nonagon, octagon, heptagon, hexagon, pentagon, decagon, prism-shape, pyramid-shape, cone-shape, any other type of polygon, equilateral triangle, right triangle, scalene triangle, obtuse triangle, acute triangle, isosceles triangle, parallelogram, rhombus, kite, trapezium, trapezoid, heart-shape, diamond-shape, crescent-shape, flower-shape, star-shape, rainbow-shape, any alphabet letter shape, animal-shape, icosahedron or a dodecahedron,
    further wherein the at least one or more adhesive elements are configured to attach to at least one area of a tampon wearer's body,
    further wherein the at least one or more adhesive elements comprise hypoallergenic material,
    further wherein the at least one or more adhesive elements are configured for transdermal delivery of one or more therapeutic agents to the at least one area of the tampon wearer's body.

2. The method of claim 1, wherein the tape dispenser is a medical grade tape dispenser.

3. The method of claim 1, wherein the one or more adhesive elements have an overall surface area that is greater than 0.001 square inches and less than 900 square inches.

4. The method of claim 1, wherein the one or more adhesive elements have an overall surface area that is greater than 0.001 square inches and less than 800 square inches.

5. The method of claim 1, wherein the one or more adhesive elements have an overall surface area that is greater than 0.001 square inches and less than 700 square inches.

6. The method of claim 1, wherein the one or more adhesive elements have an overall surface area that is greater than 0.001 square inches and less than 600 square inches.

7. The method of claim 1, wherein the one or more adhesive elements have an overall surface area that is greater than 0.001 square inches and less than 500 square inches.

8. The method of claim 1, wherein the one or more adhesive elements have an overall surface area that is greater than 0.001 square inches and less than 400 square inches.

9. The method of claim 1, wherein the one or more adhesive elements have an overall surface area that is greater than 0.001 square inches and less than 300 square inches.

10. The method of claim 1, wherein the one or more adhesive elements have an overall surface area that is greater than 0.001 square inches and less than 200 square inches.

11. The method of claim 1, wherein the one or more adhesive elements have an overall surface area that is greater than 0.001 square inches and less than 100 square inches.

12. The method of claim 1, wherein the one or more adhesive elements change color to show that it is time to discard the tampon after the tampon has been used for eight hours.

13. A kit for self-assembly of a secure tampon, wherein the kit comprises an absorbent object securely attached to at least one or more connector elements, further wherein the kit comprises at least one or more adhesive elements, wherein the at least one or more adhesive elements are configured to be securely attached to the one or more connector elements,
    wherein the one or more adhesive elements have a shape that is generally round, circular, oval, elliptical, square, rectangular, triangular, semicircle, nonagon, octagon, heptagon, hexagon, pentagon, decagon, prism-shape, pyramid-shape, cone-shape, any other type of polygon, equilateral triangle, right triangle, scalene triangle, obtuse triangle, acute triangle, isosceles triangle, parallelogram, rhombus, kite, trapezium, trapezoid, heart-shape, diamond-shape, crescent-shape, flower-shape, star-shape, rainbow-shape, any alphabet letter shape, animal-shape, icosahedron or a dodecahedron,
    further wherein the at least one or more adhesive elements are configured to attach to at least one area of a tampon wearer's body,
    further wherein the at least one or more adhesive elements comprise hypoallergenic material,
    further wherein the at least one or more adhesive elements are configured for transdermal delivery of one or more therapeutic agents to the at least one area of the tampon wearer's body.

14. The kit of claim 13, wherein the at least one or more adhesive elements comprise safe and non-toxic tape, liquid adhesive, adhesive material, waterproof tape, medical adhesive tape, pressure sensitive adhesive tape, surgical tape, paper tape, or any combination thereof.

15. The kit of claim 13, wherein the at least one or more adhesive elements comprise hydrocolloid, acrylic, polyurethane, silicone, and a backing of cloth, waterproof material, paper, pressure-sensitive tape, micropore adhesive material, or any combination thereof.

16. The kit of claim 13, wherein the one or more adhesive elements change color to show that it is time to discard the tampon after the tampon has been used for eight hours.

17. The kit of claim 13, further comprising an applicator.

18. The kit of claim 13, wherein the at least one or more adhesive elements are configured to securely attach to at least one area of the tampon wearer's body.

19. The kit of claim 13, wherein the one or more adhesive elements are configured to securely attach to any area of skin surrounding the vagina, any part of the leg or legs, inner thigh, or any area of the skin covering the pubic bone.

20. The kit of claim 13, wherein the one or more adhesive elements have an overall surface area that is greater than 0.001 square inches and less than 900 square inches.

21. The kit of claim 13, wherein the one or more adhesive elements have an overall surface area that is greater than 0.001 square inches and less than 800 square inches.

22. The kit of claim 13, wherein the one or more adhesive elements have an overall surface area that is greater than 0.001 square inches and less than 700 square inches.

23. The kit of claim 13, wherein the one or more adhesive elements have an overall surface area that is greater than 0.001 square inches and less than 600 square inches.

24. The kit of claim 13, wherein the one or more adhesive elements have an overall surface area that is greater than 0.001 square inches and less than 500 square inches.

25. The kit of claim 13, wherein the one or more adhesive elements have an overall surface area that is greater than 0.001 square inches and less than 400 square inches.

26. The kit of claim 13, wherein the one or more adhesive elements have an overall surface area that is greater than 0.001 square inches and less than 300 square inches.

27. The kit of claim 13, wherein the one or more adhesive elements have an overall surface area that is greater than 0.001 square inches and less than 200 square inches.

28. The kit of claim 13, wherein the one or more adhesive elements have an overall surface area that is greater than 0.001 square inches and less than 100 square inches.

29. The kit of claim 13, wherein the one or more adhesive elements change color to show that it is time to discard the tampon after the tampon has been used for eight hours.

30. A digital tampon, wherein the digital tampon is securely connected to one end of a connector element, further wherein an adhesive element is securely attached to another end of the connector element, further wherein the adhesive element is wrapped around the digital tampon,
wherein the adhesive element has a shape that is generally round, circular, oval, elliptical, triangular, semicircle, nonagon, octagon, heptagon, hexagon, pentagon, decagon, prism-shape, pyramid-shape, cone-shape, any other type of polygon, equilateral triangle, right triangle, scalene triangle, obtuse triangle, acute triangle, isosceles triangle, parallelogram, rhombus, kite, trapezium, trapezoid, heart-shape, diamond-shape, crescent-shape, flower-shape, star-shape, rainbow-shape, any alphabet letter shape, animal-shape, icosahedron or a dodecahedron,
further wherein the adhesive element is configured to attach to at least one area of a tampon wearer's body,
further wherein the adhesive element comprises hypoallergenic material,
further wherein the adhesive element is configured for transdermal delivery of one or more therapeutic agents to the at least one area of the tampon wearer's body.

* * * * *